US011459610B2

(12) United States Patent
Chesney et al.

(10) Patent No.: US 11,459,610 B2
(45) Date of Patent: Oct. 4, 2022

(54) COMPOSITIONS AND METHODS FOR IMPROVING SAMPLE IDENTIFICATION IN INDEXED NUCLEIC ACID LIBRARIES

(71) Applicant: Illumina Cambridge Limited, Nr Saffron Walden (GB)

(72) Inventors: Michael Chesney, Nr Saffron Walden (GB); Vincent Peter Smith, Nr Saffron Walden (GB); Claire Bevis-Mott, Nr Saffrom Walden (GB); Jonathan Mark Boutell, Nr Saffron Walden (GB); Angela Kalbande, Nr Saffron Walden (GB)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 293 days.

(21) Appl. No.: 15/960,035

(22) Filed: Apr. 23, 2018

(65) Prior Publication Data

US 2018/0305753 A1 Oct. 25, 2018

Related U.S. Application Data

(60) Provisional application No. 62/488,825, filed on Apr. 23, 2017.

(51) Int. Cl.

| | |
|---|---|
| ***C12Q 1/6874*** | (2018.01) |
| ***C12Q 1/6855*** | (2018.01) |
| ***C12N 15/10*** | (2006.01) |
| ***C40B 40/06*** | (2006.01) |
| ***C12Q 1/6806*** | (2018.01) |
| ***C40B 50/16*** | (2006.01) |
| ***C40B 50/18*** | (2006.01) |
| ***C12Q 1/6809*** | (2018.01) |
| ***C12Q 1/6816*** | (2018.01) |
| ***C12Q 1/6834*** | (2018.01) |
| *C40B 20/04* | (2006.01) |
| *C40B 70/00* | (2006.01) |
| *C40B 80/00* | (2006.01) |

(52) U.S. Cl.

CPC ....... *C12Q 1/6874* (2013.01); *C12N 15/1065* (2013.01); *C12Q 1/6806* (2013.01); *C12Q 1/6809* (2013.01); *C12Q 1/6816* (2013.01); *C12Q 1/6834* (2013.01); *C12Q 1/6855* (2013.01); *C40B 40/06* (2013.01); *C40B 20/04* (2013.01); *C40B 50/16* (2013.01); *C40B 50/18* (2013.01); *C40B 70/00* (2013.01); *C40B 80/00* (2013.01)

(58) Field of Classification Search

None

See application file for complete search history.

(56) References Cited

U.S. PATENT DOCUMENTS

| | | | | |
|---|---|---|---|---|
| 7,741,463 | B2 | 6/2010 | Gormley et al. | |
| 8,053,192 | B2 | 11/2011 | Bignell et al. | |
| 8,182,989 | B2 | 5/2012 | Bignell et al. | |
| 8,822,150 | B2 | 9/2014 | Bignell et al. | |
| 8,895,249 | B2 | 11/2014 | Shen et al. | |
| 9,169,513 | B2 | 10/2015 | Shen et al. | |
| 9,512,478 | B2 | 12/2016 | Bignell et al. | |
| 9,758,816 | B2 | 9/2017 | Shen et al. | |
| 2002/0192769 | A1* | 12/2002 | Park et al. | C12Q 1/686 435/91.2 |
| 2004/0209299 | A1 | 10/2004 | Pinter et al. | |
| 2006/0292611 | A1 | 12/2006 | Berka et al. | |
| 2009/0233291 | A1 | 9/2009 | Chen | |
| 2010/0062494 | A1 | 3/2010 | Church et al. | |
| 2013/0231253 | A1 | 9/2013 | Amorese et al. | |
| 2014/0000663 | A1 | 3/2014 | Gormley et al. | |
| 2015/0051116 | A1 | 2/2015 | Kim | |
| 2015/0265995 | A1 | 9/2015 | Head et al. | |
| 2016/0000173 | A1 | 1/2016 | Arnold et al. | |
| 2016/0090623 | A1 | 3/2016 | Rigatti et al. | |
| 2016/0186249 | A1 | 6/2016 | Becker et al. | |
| 2016/0355880 | A1 | 12/2016 | Gormley et al. | |
| 2017/0088833 | A1* | 3/2017 | Joung et al. | C12Q 1/6855 |
| 2018/0305750 | A1 | 10/2018 | Smith et al. | |
| 2018/0305751 | A1 | 10/2018 | Vermaas et al. | |
| 2018/0305752 | A1 | 10/2018 | Vermaas et al. | |
| 2018/0305753 | A1 | 10/2018 | Chesney et al. | |

FOREIGN PATENT DOCUMENTS

| | | | |
|---|---|---|---|
| EP | 1 256 630 | A2 | 11/2002 |
| WO | WO 2007/052006 | A1 | 5/2007 |
| WO | 2009098037 | A1 | 8/2009 |
| WO | WO 2011/112534 | A1 | 9/2011 |
| WO | WO 2013/177220 | A1 | 11/2013 |

(Continued)

OTHER PUBLICATIONS

International Search Report and Written Opinion for International Patent Application No. PCT/IB2018/000497 dated Jun. 29, 2018, 14 pages.

International Search Report and Written Opinion for International Patent Application No. PCT/IB2018/000509, dated Sep. 12, 2018, 14 pages.

International Search Report and Written Opinion for International Patent Application No. PCT/US2018/028867, dated Jun. 28, 2018, 15 pages.

International Search Report and Written Opinion for International Patent Application No. PCT/US2018/028881, dated Jun. 28, 2018, 14 pages.

"Effects of Index Misassignment on Multiplexing and Downstream Analysis," Illumina, Inc., 2017, Pub. No. 770-2017-004-A, 4 pages.

(Continued)

*Primary Examiner* — Kaijiang Zhang

(74) *Attorney, Agent, or Firm* — Mueting Raasch Group

(57) ABSTRACT

The present invention is concerned with compositions and methods for improving the rate of correct sample identification in indexed nucleic acid library preparations for multiplex next generation sequencing by exonuclease treatment and optionally blocking the 3' ends of pooled indexed polynucleotides from multiple samples prior to amplification and sequencing.

25 Claims, 12 Drawing Sheets

(56) References Cited

FOREIGN PATENT DOCUMENTS

| | | | |
|---|---|---|---|
| WO | WO 2015/069374 | A1 | 5/2015 |
| WO | WO 2016/130704 | A2 | 8/2016 |
| WO | 2018144216 | A1 | 8/2018 |
| WO | WO 2018/197945 | A1 | 11/2018 |
| WO | WO 2018/197950 | A1 | 11/2018 |
| WO | WO 2018/200380 | A1 | 11/2018 |
| WO | WO 2018/200386 | A1 | 11/2018 |

OTHER PUBLICATIONS

Esling et al., "Accurate multiplexing and filtering for high-throughput amplicon-sequencing," *Nucleic Acids Research*, Mar. 11, 2015, Epub Feb. 17, 2015; 43(5):2513-2524.

Kircher et al., "Double indexing overcomes inaccuracies in multiplex sequencing on the Illumina platform," *Nucleic Acids Research*, Jan. 1, 2012, Epub Oct. 21, 2011; XP002751968, 40(1):e3-1, 8 pages.

Kircher et al., "Double indexing overcomes inaccuracies in multiplex sequencing on the Illumina platform," *Nucleic Acids Research, Supplementary Tables*, Jan. 1, 2012, Epub Oct. 21, 2011; XP055476349, 40(1):e3-e3, 17 pages.

Sinha et al., "Index switching causes "spreading-of-signal" among multiplexed samples in Illumina HiSeq 4000 DNA sequencing," *bioRxiv*, Apr. 9, 2017, XP055483189, 29 pages.

Ambardar et al., "High Throughput Sequencing: An Overview of Sequencing Chemistry" Jul. 2016 *Indian J Microbiol*, 56(4):394-404.

European Search Report for application No. EP21183272 dated Oct. 20, 2021, 9 pages.

* cited by examiner 12 different P7 Indices; 8 different P5 Indices

| | 1 | 2 | 3 | 4 | 5 | 6 | 7 | 8 | 9 | 10 | 11 | 12 |
|---|---|---|---|---|---|---|---|---|---|---|---|---|
| A | D701-D501 | D702-D501 | D703-D501 | D704-D501 | D705-D501 | D706-D501 | D707-D501 | D708-D501 | D709-D501 | D710-D501 | D711-D501 | D712-D501 |
| B | D701-D502 | D702-D502 | D703-D502 | D704-D502 | D705-D502 | D706-D502 | D707-D502 | D708-D502 | D709-D502 | D710-D502 | D711-D502 | D712-D502 |
| C | D701-D503 | D702-D503 | D703-D503 | D704-D503 | D705-D503 | D706-D503 | D707-D503 | D708-D503 | D709-D503 | D710-D503 | D711-D503 | D712-D503 |
| D | D701-D504 | D702-D504 | D703-D504 | D704-D504 | D705-D504 | D706-D504 | D707-D504 | D708-D504 | D709-D504 | D710-D504 | D711-D504 | D712-D504 |
| E | D701-D505 | D702-D505 | D703-D505 | D704-D505 | D705-D505 | D706-D505 | D707-D505 | D708-D505 | D709-D505 | D710-D505 | D711-D505 | D712-D505 |
| F | D701-D506 | D702-D506 | D703-D506 | D704-D506 | D705-D506 | D706-D506 | D707-D506 | D708-D506 | D709-D506 | D710-D506 | D711-D506 | D712-D506 |
| G | D701-D507 | D702-D507 | D703-D507 | D704-D507 | D705-D507 | D706-D507 | D707-D507 | D708-D507 | D709-D507 | D710-D507 | D711-D507 | D712-D507 |
| H | D701-D508 | D702-D508 | D703-D508 | D704-D508 | D705-D508 | D706-D508 | D707-D508 | D708-D508 | D709-D508 | D710-D508 | D711-D508 | D712-D508 |

FIG. 10A i7 Index i5 Index

| | 701 | 702 | 703 | 704 | 705 | 706 | 707 | 708 | 709 | 710 | 711 | 712 |
|---|---|---|---|---|---|---|---|---|---|---|---|---|
| 501 | X | | | | | | | | | | | |
| 502 | | X | | | | | | | | | | |
| 503 | | | X | | | | | | | | | |
| 504 | | | | X | | | | | | | | |
| 505 | | | X | | X | | | | | | | |
| 506 | | | | | | X | | | | | | |
| 507 | | | | | | | X | | | | | |
| 508 | | | | | | | | X | | | | |

Unexpected index combination

FIG. 10B

COMPOSITIONS AND METHODS FOR IMPROVING SAMPLE IDENTIFICATION IN INDEXED NUCLEIC ACID LIBRARIES

CROSS-REFERENCE TO RELATED APPLICATIONS

This application claims the benefit of U.S. Provisional Application Ser. No. 62/488,825, filed Apr. 23, 2017, which is incorporated by reference herein.

FIELD

The present disclosure relates to, among other things, sequencing of polynucleotides from multiple libraries; and more particularly to increasing the likelihood that sequencing properly identifies the library from which the polynucleotides originated.

BACKGROUND

Improvements in next-generation sequencing (NGS) technology have greatly increased sequencing speed and data output, resulting in the massive sample throughput of current sequencing platforms. Approximately 10 years ago, the Illumina Genome Analyzer was capable of generating up to 1 gigabyte of sequence data per run. Today, the Illumina NovaSeg™ Series of Systems are capable of generating up to 2 terabytes of data in two days, which represents a greater than 2000× increase in capacity.

One aspect of realizing this increased capacity is multiplexing, which adds unique sequences, called indexes, to each DNA fragment during library preparation. This allows large numbers of libraries to be pooled and sequenced simultaneously during a single sequencing run. Gains in throughput from multiplexing come with an added layer of complexity, as sequencing reads from pooled libraries need to be identified and sorted computationally in a process called demultiplexing before final data analysis. Index misassignment between multiplexed libraries is a known issue that has impacted NGS technologies from the time sample multiplexing was developed (Kircher et al., 2012, *Nucleic Acids Res*., Vol. 40, No. 1).

SUMMARY OF THE APPLICATION

Index hopping or jumping is observed when sequenced DNA library molecules contain a different index sequence than was present in the library adaptor during library preparation. Index hopping can occur during sample preparation or during cluster amplification of pooled multiplexed libraries. One mechanism that causes index hopping involves the presence of free unligated adaptor molecules present after library preparation.

Without intending to be limited by theory, the problem of index jumping has multiple modes, some of which involve the presence of residual unligated adaptor molecules and/or incomplete products left over from library preparation. One class of index jumping can be caused by free unligated adaptor molecules having a specific universal primer extension sequence, e.g., P7', present in the library pool, that can contribute to the formation of libraries with swapped indices. This problem can be prevented by use of a 5' exonuclease that specifically targets the P7' adaptor strand for degradation. This can be achieved, for instance, through the use of an exonuclease that is biased toward digestion of double-stranded 5' ends, or through the use of 5' end modifications to bias towards exonuclease-mediated degradation of the adaptor DNA molecules.

In one embodiment, free unligated P7' adaptor molecules present after library preparation can anneal to the immobilized surface P7 primer on a substrate such as a flow cell and serve as a template for generation of a longer, modified immobilized surface primer that contains a specific index sequence, e.g., i7, and a common universal primer binding sequence. The modified surface primer would then have complementarity to library molecules in the adaptor region 3' of the index molecule, allowing the generation of surface-bound library molecule with a different i7 index sequence than was present in the original library molecule.

This mechanism of index jumping can be reduced or eliminated through the use of 5' exonucleases to selectively degrade unligated P7' adaptor molecules. One mode of selective degradation involves the use of a 5' exonuclease with 5' to 3' exonuclease activity that is biased toward degradation of double stranded DNA molecules. This approach could be used in the context of a library preparation method using forked adaptors, with one double stranded end (possibly containing a short 3' overhang), and a "forked" single stranded end. After ligation to sample insert libraries, the resultant library contains single-stranded "forked" regions on both ends. Some unligated adaptor molecules remain that include the double stranded end. The P7' strand of this adaptor molecule can then be targeted for degradation through the use of a 5' to 3' exonuclease that is biased toward digestion of double stranded DNA. Use of a 5' to 3' exonuclease that selectively targets a 5' phosphorylated double stranded end aids in narrowing the activity of the exonuclease to unligated adaptors.

Another mode of selective degradation involves the use of a 5' exonuclease with 5' to 3' exonuclease activity and 3' to 5' DNA exonuclease activity. This approach could also be used in the context of a library preparation method using forked adaptors, with one double stranded end (possibly containing a short 3' overhang), and a "forked" single stranded end. After ligation to sample insert libraries, some unligated adaptor molecules remain that include the double stranded end. The P7' strand of this adaptor molecule can then be targeted for degradation through the use of 5' exonuclease with 5' to 3' exonuclease activity and 3' to 5' DNA exonuclease activity, but the 3' to 5' DNA exonuclease activity can be reduced by the use of a modification at each of the 3' ends of an adapter to block the 3' to 5' exonuclease activity. This modification prevents digestion of adaptor-target-adaptor molecules from the free 3' ends. An optional modification is at the 5' "forked" single stranded end. This modification prevents digestion of adaptor-target-adaptor molecules from the free 5' ends.

One class of index jumping can be caused by incomplete products present in the library pool. During library production incomplete species can result, such as adaptor-target molecules which do not include the desired structure of a target molecule flanked on each end by adaptor molecules, and target molecules which do not have an adaptor molecule attached at either end. These species can contribute to the formation of libraries with swapped indices by acting as primers for unwanted extension reactions.

This mechanism of index jumping can be reduced or eliminated through the use of exonucleases having 3' to 5' exonuclease activity to selectively degrade incomplete products present in the library pool. This approach could also be used in the context of a library preparation method using forked adaptors, with one double stranded end (possibly containing a short 3' overhang), and a "forked" single stranded end. After ligation to sample insert libraries, some incomplete products remain that include either a double stranded end and a "forked" single stranded end, or two double stranded ends. These double stranded ends can be targeted for degradation through the use of an exonuclease having 3' to 5' exonuclease activity that is biased towards double stranded DNA molecules. Use of a 3' to 5' exonuclease that selectively targets blunt or recessed 3' termini can aid in narrowing the activity of the exonuclease to the incomplete products.

One class of index jumping can be caused by free unligated adaptor molecules having a specific universal primer extension sequence, e.g., P7', present in the library pool, or incomplete products, such as adaptor-target molecules which do not include a target polynucleotide flanked by on each end by adaptor molecules, that can contribute to the formation of libraries with swapped indices by acting as primers for unwanted extension reactions. This problem can be prevented introducing 3' blocks into free unligated adaptor molecules having a specific universal primer extension sequence, e.g., P7', or incomplete products present in the library pool.

Provided herein are compositions and methods for mitigating index hopping and its effect on sequencing data quality.

As used herein, the term "each," when used in reference to a collection of items, is intended to identify an individual item in the collection but does not necessarily refer to every item in the collection unless the context clearly dictates otherwise.

As used herein, the term "nucleic acid" is intended to be consistent with its use in the art and includes naturally occur ring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain any of a variety of analogs of these sugar moieties that are known in the art. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid are known in the art. The term "target," when used in reference to a nucleic acid, is intended as a semantic identifier for the nucleic acid in the context of a method or composition set forth herein and does not necessarily limit the structure or function of the nucleic acid beyond what is otherwise explicitly indicated.

As used herein, the term "transport" refers to movement of a molecule through a fluid. The term can include passive transport such as movement of molecules along their concentration gradient (e.g. passive diffusion). The term can also include active transport whereby molecules can move along their concentration gradient or against their concentration gradient. Thus, transport can include applying energy to move one or more molecule in a desired direction or to a desired location such as an amplification site.

As used herein, the term "universal sequence" refers to a region of sequence that is common to two or more nucleic acid molecules, e.g., adaptor-target adaptor molecules, where the molecules also have regions of sequence that differ from each other. A universal sequence that is present in different members of a collection of molecules can allow capture of multiple different nucleic acids using a population of universal capture nucleic acids that are complementary to a portion of the universal sequence, e.g., a universal extension primer binding site. Non-limiting examples of universal extension primer binding sites include sequences that are identical to or complementary to P5 and P7 primers. Similarly, a universal sequence present in different members of a collection of molecules can allow the replication or amplification of multiple different nucleic acids using a population of universal primers that are complementary to a portion of the universal sequence, e.g., a universal primer binding site. Thus a universal capture nucleic acid or a universal primer includes a sequence that can hybridize specifically to a universal sequence. Target nucleic acid molecules may be modified to attach universal adapters (also referred to herein as adapters), for example, at one or both ends of the different target sequences, as described herein.

The terms "P5" and "P7" may be used when referring to amplification primers, e.g., universal primer extension primers. The terms "P5'" (P5 prime) and "P7'" (P7 prime) refer to the complement of P5 and P7, respectively. It will be understood that any suitable amplification primers can be used in the methods presented herein, and that the use of P5 and P7 are exemplary embodiments only. Uses of amplification primers such as P5 and P7 on flowcells is known in the art, as exemplified by the disclosures of WO 2007/010251, WO 2006/064199, WO 2005/065814, WO 2015/106941, WO 1998/044151, and WO 2000/018957. For example, any suitable forward amplification primer, whether immobilized or in solution, can be useful in the methods presented herein for hybridization to a complementary sequence and amplification of a sequence. Similarly, any suitable reverse amplification primer, whether immobilized or in solution, can be useful in the methods presented herein for hybridization to a complementary sequence and amplification of a sequence. One of skill in the art will understand how to design and use primer sequences that are suitable for capture, and amplification of nucleic acids as presented herein.

As used herein, "amplify", "amplifying" or "amplification reaction" and their derivatives, refer generally to any action or process whereby at least a portion of a nucleic acid molecule is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. Amplification optionally includes linear or exponential replication of a nucleic acid molecule. In some embodiments, such amplification can be performed using isothermal conditions; in other embodiments, such amplification can include thermocycling. In some embodiments, the amplification is a multiplex amplification that includes the simultaneous amplification of a plurality of target sequences in a single amplification reaction. In some embodiments, "amplification" includes amplification of at least some portion of DNA and RNA based nucleic acids alone, or in combination. The amplification reaction can include any of the amplification processes known to one of ordinary skill in the art. In some embodiments, the amplification reaction includes polymerase chain reaction (PCR).

As used herein, "amplification conditions" and its derivatives, generally refers to conditions suitable for amplifying one or more nucleic acid sequences. Such amplification can be linear or exponential. In some embodiments, the amplification conditions can include isothermal conditions or alternatively can include thermocycling conditions, or a combination of isothermal and thermocycling conditions. In some embodiments, the conditions suitable for amplifying one or more nucleic acid sequences include polymerase chain reaction (PCR) conditions. Typically, the amplification conditions refer to a reaction mixture that is sufficient to amplify nucleic acids such as one or more target sequences, or to amplify an amplified target sequence ligated to one or more adapters, e.g., an adapter-ligated amplified target sequence. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as $Mg^{2+}$ or $Mn^{2+}$ and can also include various modifiers of ionic strength.

As used herein, "re-amplification" and their derivatives refer generally to any process whereby at least a portion of an amplified nucleic acid molecule is further amplified via any suitable amplification process (referred to in some embodiments as a "secondary" amplification), thereby producing a reamplified nucleic acid molecule. The secondary amplification need not be identical to the original amplification process whereby the amplified nucleic acid molecule was produced; nor need the reamplified nucleic acid molecule be completely identical or completely complementary to the amplified nucleic acid molecule; all that is required is that the reamplified nucleic acid molecule include at least a portion of the amplified nucleic acid molecule or its complement. For example, the re-amplification can involve the use of different amplification conditions and/or different primers, including different target-specific primers than the primary amplification.

As used herein, the term "polymerase chain reaction" ("PCR") refers to the method of Mullis U.S. Pat. Nos. 4,683,195 and 4,683,202, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a series of thermal cycling in the presence of a DNA polymerase. The two primers are complementary to their respective strands of the double stranded polynucleotide of interest. The mixture is denatured at a higher temperature first and the primers are then annealed to complementary sequences within the polynucleotide of interest molecule. Following annealing, the primers are extended with a polymerase to form a new pair of complementary strands. The steps of denaturation, primer annealing and polymerase extension can be repeated many times (referred to as thermocycling) to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". In a modification to the method discussed above, the target nucleic acid molecules can be PCR amplified using a plurality of different primer pairs, in some cases, one or more primer pairs per target nucleic acid molecule of interest, thereby forming a multiplex PCR reaction.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy can be about 12-plex, 24-plex, 48-plex, 96-plex, 192-plex, 384-plex, 768-plex, 1536-plex, 3072-plex, 6144-plex or higher. It is also possible to detect the amplified target sequences by several different methodologies (e.g., gel electrophoresis followed by densitometry, quantitation with a bioanalyzer or quantitative PCR, hybridization with a labeled probe; incorporation of biotinylated primers followed by avidin-enzyme conjugate detection; incorporation of 32P-labeled deoxynucleotide triphosphates into the amplified target sequence).

As used herein, the term "primer" and its derivatives refer generally to any polynucleotide that can hybridize to a target sequence of interest. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer may be comprised of any combination of nucleotides or analogs thereof. In some embodiments, the primer is a single-stranded oligonucleotide or polynucleotide. The terms "polynucleotide" and "oligonucleotide" are used interchangeably herein to refer to a polymeric form of nucleotides of any length, and may comprise ribonucleotides, deoxyribonucleotides, analogs thereof, or mixtures thereof. The terms should be understood to include, as equivalents, analogs of either DNA or RNA made from nucleotide analogs and to be applicable to single stranded (such as sense or antisense) and double stranded polynucleotides. The term as used herein also encompasses cDNA, that is complementary or copy DNA produced from an RNA template, for example by the action of reverse transcriptase. This term refers only to the primary structure of the molecule. Thus, the term includes triple-, double- and single-stranded deoxyribonucleic acid ("DNA"), as well as triple-, double- and single-stranded ribonucleic acid ("RNA").

As used herein, "amplified target sequences" and its derivatives, refers generally to a nucleic acid sequence produced by the amplifying the target sequences using target-specific primers and the methods provided herein. The amplified target sequences may be either of the same sense (i.e. the positive strand) or antisense (i.e., the negative strand) with respect to the target sequences.

As used herein, the terms "ligating", "ligation" and their derivatives refer generally to the process for covalently linking two or more molecules together, for example covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, the ligation can include forming a covalent bond between a 5' phosphate group of one nucleic acid and a 3' hydroxyl group of a second nucleic acid thereby forming a ligated nucleic acid molecule. Generally for the purposes of this disclosure, an amplified target sequence can be ligated to an adapter to generate an adapter-ligated amplified target sequence. The skilled person will recognize that a ligation reaction may not result in linking all molecules present in the reaction.

As used herein, "ligase" and its derivatives, refers generally to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but not limited to, T4 DNA ligase, T4 RNA ligase, and *E. coli* DNA ligase.

As used herein, "ligation conditions" and its derivatives, generally refers to conditions suitable for ligating two molecules to each other. In some embodiments, the ligation conditions are suitable for sealing nicks or gaps between nucleic acids. As used herein, the term nick or gap is consistent with the use of the term in the art. Typically, a nick or gap can be ligated in the presence of an enzyme, such as ligase at an appropriate temperature and pH. In some embodiments, T4 DNA ligase can join a nick between nucleic acids at a temperature of about 70-72° C.

As used herein, the term "adapter" and its derivatives, e.g., universal adapter, refers generally to any linear oligonucleotide which can be ligated to a nucleic acid molecule of the disclosure. In some embodiments, the adapter is substantially non-complementary to the 3' end or the 5' end of any target sequence present in the sample. In some embodiments, suitable adapter lengths are in the range of about 10-100 nucleotides, about 12-60 nucleotides and about 15-50 nucleotides in length. Generally, the adapter can include any combination of nucleotides and/or nucleic acids. In some aspects, the adapter can include one or more cleavable groups at one or more locations. In another aspect, the adapter can include a sequence that is substantially identical, or substantially complementary, to at least a portion of a primer, for example a universal primer. In some embodiments, the adapter can include a barcode or tag to assist with downstream error correction, identification or sequencing.

The terms "adaptor" and "adapter" are used interchangeably.

The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., *Nature* 456:53-59 (2008), WO 04/018497; U.S. Pat. No. 7,057,026; WO 91/06678; WO 07/123744; U.S. Pat. No. 7,329,492; U.S. Pat. No. 7,211,414; U.S. Pat. No. 7,315,019; U.S. Pat. No. 7,405,281, and US 2008/0108082, each of which is incorporated herein by reference.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "amplification site" refers to a site in or on an array where one or more amplicons can be generated. An amplification site can be further configured to contain, hold or attach at least one amplicon that is generated at the site.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "capacity," when used in reference to a site and nucleic acid material, means the maximum amount of nucleic acid material that can occupy the site. For example, the term can refer to the total number of nucleic acid molecules that can occupy the site in a particular condition. Other measures can be used as well including, for example, the total mass of nucleic acid material or the total number of copies of a particular nucleotide sequence that can occupy the site in a particular condition. Typically, the capacity of a site for a target nucleic acid will be substantially equivalent to the capacity of the site for amplicons of the target nucleic acid.

As used herein, the term "capture agent" refers to a material, chemical, molecule or moiety thereof that is capable of attaching, retaining or binding to a target molecule (e.g. a target nucleic acid). Exemplary capture agents include, without limitation, a capture nucleic acid that is complementary to at least a portion of a target nucleic acid, a member of a receptor-ligand binding pair (e.g. avidin, streptavidin, biotin, lectin, carbohydrate, nucleic acid binding protein, epitope, antibody, etc.) capable of binding to a target nucleic acid (or linking moiety attached thereto), or a chemical reagent capable of forming a covalent bond with a target nucleic acid (or linking moiety attached thereto).

As used herein, the term "clonal population" refers to a population of nucleic acids that is homogeneous with respect to a particular nucleotide sequence. The homogenous sequence is typically at least 10 nucleotides long, but can be even longer including for example, at least 50, 100, 250, 500 or 1000 nucleotides long. A clonal population can be derived from a single target nucleic acid or template nucleic acid. Typically, all of the nucleic acids in a clonal population will have the same nucleotide sequence. It will be understood that a small number of mutations (e.g. due to amplification artifacts) can occur in a clonal population without departing from clonality.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

BRIEF DESCRIPTION OF THE FIGURES

The following detailed description of specific embodiments of the present disclosure may be best understood when read in conjunction with the following drawings.

FIG. 9A shows how reads from a given sample are incorrectly demultiplexed and mixed with a different sample following demultiplexing. FIG. 9B demonstrates index hopping in a dual index system, where it leads to unexpected combinations of index tag sequences.

FIGS. 10A and 10B illustrate the general approach to measuring the rate of index hopping in a given system. FIG. 10A shows an exemplary layout of a dual adapter plate, wherein each individual well of a 96-well plate contains a unique pair of index tag sequences. FIG. 10B shows an experimental setup aimed at measuring the rate of index hopping, wherein only unique dual index tag combinations are used.

FIG. 11A shows a 6-fold increase in index hopping associated with a 50% spike-in of free adapters. FIG. 11B shows an approximately linear effect of the free forked adapter on the rate of index hopping within the range tested.

FIG. 13 shows the effect of combined exonuclease and 3' blocking treatment according to the present invention on the rates of index hopping in Illumina TruSeq® PCR-Free library preparation work flow, with and without a free adapter spike-in.

Figure 1:
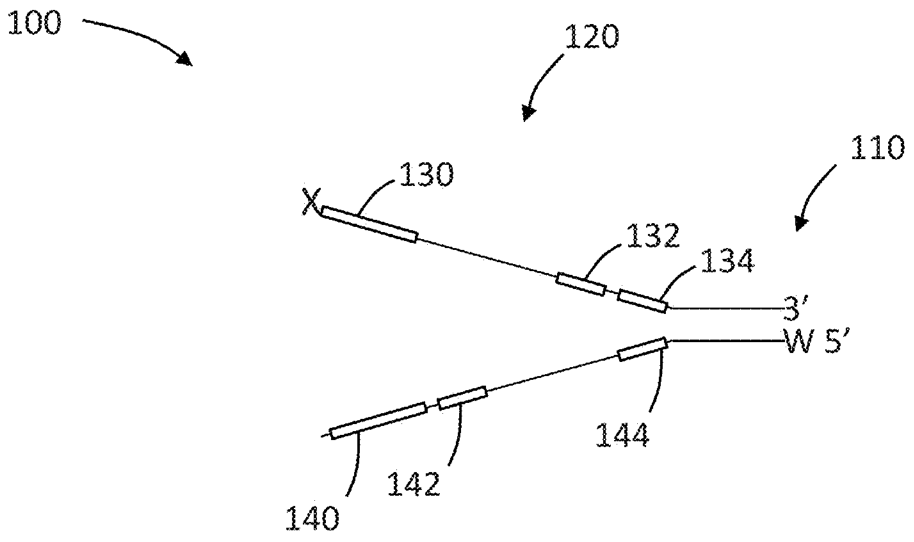
FIGS. 1, 2, 3 and 4 are schematic drawings of multiple embodiments of an adapter according to various aspects of the disclosure presented herein.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Provided herein are compositions and methods, e.g., methods for making a library, for mitigating the impact of index hopping on sequencing data quality.

Double-Stranded Target Fragments

In one embodiment, a composition includes a plurality of double-stranded target fragments. The terms "target fragment," "target nucleic acid fragment, "target molecule," "target nucleic acid molecule," and "target nucleic acid" are used interchangeably to refer to nucleic acid molecules that it is desired to sequence, such as on an array. The target nucleic acid may be essentially any nucleic acid of known or unknown sequence. It may be, for example, a fragment of genomic DNA or cDNA. Sequencing may result in determination of the sequence of the whole, or a part of the target molecule. The targets can be derived from a primary nucleic acid sample that has been randomly fragmented. In one embodiment, the targets can be processed into templates suitable for amplification by the placement of universal amplification sequences, e.g., sequences present in a universal adaptor, at the ends of each target fragment. The targets can also be obtained from a primary RNA sample by reverse transcription into cDNA.

The primary nucleic acid sample may originate in double-stranded DNA (dsDNA) form (e.g. genomic DNA fragments, PCR and amplification products and the like) from a sample or may have originated in single-stranded form from a sample, as DNA or RNA, and been converted to dsDNA form. By way of example, mRNA molecules may be copied into double-stranded cDNAs suitable for use in the method described herein using standard techniques well known in the art. The precise sequence of the polynucleotide molecules from a primary nucleic acid sample is generally not material to the invention, and may be known or unknown.

In one embodiment, the polynucleotide molecules from a primary nucleic acid sample are RNA molecules. In an aspect of this embodiment, RNA isolated from specific samples is first converted to double-stranded DNA using techniques known in the art. In accordance with the present disclosure the double-stranded DNA, regardless of whether it was isolated as RNA or DNA, is then tagged or indexed with a sample-specific tag. Typically, a sample-specific tag is present as part of a universal adaptor. Different preparations of such double-stranded DNA including sample-specific tags can be generated, in parallel, from RNA isolated from different specific samples. Subsequently, different preparations of double-stranded DNA including different sample-specific tags can be mixed, sequenced en masse, and the identity of each sequenced target fragment determined with respect to the sample from which it was isolated/derived by virtue of the presence of a sample-specific tag. Under certain conditions, index hopping results in sample-specific tags marking different sources being mixed or combined so a single target fragment has, for instance, a sample-specific tag identifying one source at one end, and a sample-specific tag identifying different source at the other end. This can result in sample cross contamination which can confound results of sequencing experiments. The methods described herein reduce index hopping.

In one embodiment, the primary polynucleotide molecules from a primary nucleic acid sample are DNA molecules. More particularly, the primary polynucleotide molecules represent the entire genetic complement of an organism, and are genomic DNA molecules which include both intron and exon sequences, as well as non-coding regulatory sequences such as promoter and enhancer sequences. In one embodiment, particular sub-sets of polynucleotide sequences or genomic DNA can be used, such as, for example, particular chromosomes. Yet more particularly, the sequence of the primary polynucleotide molecules is not known. Still yet more particularly, the primary polynucleotide molecules are human genomic DNA molecules. The DNA target fragments may be treated chemically or enzymatically either prior or subsequent to any random fragmentation processes, and prior or subsequent to the ligation of the universal adapter sequences.

As defined herein, "sample" and its derivatives, is used in its broadest sense and includes any specimen, culture and the like that is suspected of including a target. In some embodiments, the sample comprises DNA, RNA, PNA, LNA, chimeric or hybrid forms of nucleic acids. The sample can include any biological, clinical, surgical, agricultural, atmospheric or aquatic-based specimen containing one or more nucleic acids. The term also includes any isolated nucleic acid sample such a genomic DNA, fresh-frozen or formalin-fixed paraffin-embedded nucleic acid specimen. It is also envisioned that the sample can be from a single individual, a collection of nucleic acid samples from genetically related members, nucleic acid samples from genetically unrelated members, nucleic acid samples (matched) from a single individual such as a tumor sample and normal tissue sample, or sample from a single source that contains two distinct forms of genetic material such as maternal and fetal DNA obtained from a maternal subject, or the presence of contaminating bacterial DNA in a sample that contains plant or animal DNA. In some embodiments, the source of nucleic acid material can include nucleic acids obtained from a newborn, for example as typically used for newborn screening.

The nucleic acid sample can include high molecular weight material such as genomic DNA (gDNA). The sample can include low molecular weight material such as nucleic acid molecules obtained from FFPE or archived DNA samples. In another embodiment, low molecular weight material includes enzymatically or mechanically fragmented DNA. The sample can include cell-free circulating DNA. In some embodiments, the sample can include nucleic acid molecules obtained from biopsies, tumors, scrapings, swabs, blood, mucus, urine, plasma, semen, hair, laser capture micro-dissections, surgical resections, and other clinical or laboratory obtained samples. In some embodiments, the sample can be an epidemiological, agricultural, forensic or pathogenic sample. In some embodiments, the sample can include nucleic acid molecules obtained from an animal such as a human or mammalian source. In another embodiment, the sample can include nucleic acid molecules obtained from a non-mammalian source such as a plant, bacteria, virus or fungus. In some embodiments, the source of the nucleic acid molecules may be an archived or extinct sample or species.

Further, the methods and compositions disclosed herein may be useful to amplify a nucleic acid sample having low-quality nucleic acid molecules, such as degraded and/or fragmented genomic DNA from a forensic sample. In one embodiment, forensic samples can include nucleic acids obtained from a crime scene, nucleic acids obtained from a missing persons DNA database, nucleic acids obtained from a laboratory associated with a forensic investigation or include forensic samples obtained by law enforcement agencies, one or more military services or any such personnel. The nucleic acid sample may be a purified sample or a crude DNA containing lysate, for example derived from a buccal swab, paper, fabric or other substrate that may be impregnated with saliva, blood, or other bodily fluids. As such, in some embodiments, the nucleic acid sample may comprise low amounts of, or fragmented portions of DNA, such as genomic DNA. In some embodiments, target sequences can be present in one or more bodily fluids including but not limited to, blood, sputum, plasma, semen, urine and serum. In some embodiments, target sequences can be obtained from hair, skin, tissue samples, autopsy or remains of a victim. In some embodiments, nucleic acids including one or more target sequences can be obtained from a deceased animal or human. In some embodiments, target sequences can include nucleic acids obtained from non-human DNA such a microbial, plant or entomological DNA. In some embodiments, target sequences or amplified target sequences are directed to purposes of human identification. In some embodiments, the disclosure relates generally to methods for identifying characteristics of a forensic sample. In some embodiments, the disclosure relates generally to human identification methods using one or more target specific primers disclosed herein or one or more target specific primers designed using the primer design criteria outlined herein. In one embodiment, a forensic or human identification sample containing at least one target sequence can be amplified using any one or more of the target-specific primers disclosed herein or using the primer criteria outlined herein.

Additional non-limiting examples of sources of biological samples can include whole organisms as well as a sample obtained from a patient. The biological sample can be obtained from any biological fluid or tissue and can be in a variety of forms, including liquid fluid and tissue, solid tissue, and preserved forms such as dried, frozen, and fixed forms. The sample may be of any biological tissue, cells or fluid. Such samples include, but are not limited to, sputum, blood, serum, plasma, blood cells (e.g., white cells), ascitic fluid, urine, saliva, tears, sputum, vaginal fluid (discharge), washings obtained during a medical procedure (e.g., pelvic or other washings obtained during biopsy, endoscopy or surgery), tissue, nipple aspirate, core or fine needle biopsy samples, cell-containing body fluids, free floating nucleic acids, peritoneal fluid, and pleural fluid, or cells therefrom. Biological samples may also include sections of tissues such as frozen or fixed sections taken for histological purposes or micro-dissected cells or extracellular parts thereof. In some embodiments, the sample can be a blood sample, such as, for example, a whole blood sample. In another example, the sample is an unprocessed dried blood spot (DBS) sample. In yet another example, the sample is a formalin-fixed paraffin-embedded (FFPE) sample. In yet another example, the sample is a saliva sample. In yet another example, the sample is a dried saliva spot (DSS) sample.

Random fragmentation refers to the fragmentation of a polynucleotide molecule from a primary nucleic acid sample in a non-ordered fashion by enzymatic, chemical or mechanical means. Such fragmentation methods are known in the art and use standard methods (Sambrook and Russell, Molecular Cloning, A Laboratory Manual, third edition). In one embodiment, the fragmentation uses methods disclosed in Gunderson et al. (WO 2016/130704). For the sake of clarity, generating smaller fragments of a larger piece of nucleic acid via specific PCR amplification of such smaller fragments is not equivalent to fragmenting the larger piece of nucleic acid because the larger piece of nucleic acid sequence remains in intact (i.e., is not fragmented by the PCR amplification). Moreover, random fragmentation is designed to produce fragments irrespective of the sequence identity or position of nucleotides comprising and/or surrounding the break. More particularly, the random fragmentation is by mechanical means such as nebulization or sonication to produce fragments of about 50 base pairs in length to about 1500 base pairs in length, still more particularly 50-700 base pairs in length, yet more particularly 50-400 base pairs in length. Most particularly, the method is used to generate smaller fragments of from 50-150 base pairs in length Fragmentation of polynucleotide molecules by mechanical means (nebulization, sonication and Hydroshear, for example) results in fragments with a heterogeneous mix of blunt and 3'- and 5'-overhanging ends. It is therefore desirable to repair the fragment ends using methods or kits (such as the Lucigen DNA terminator End Repair Kit) known in the art to generate ends that are optimal for insertion, for example, into blunt sites of cloning vectors. In a particular embodiment, the fragment ends of the population of nucleic acids are blunt ended. More particularly, the fragment ends are blunt ended and phosphorylated. The phosphate moiety can be introduced via enzymatic treatment, for example, using polynucleotide kinase.

In a particular embodiment, the target fragment sequences are prepared with single overhanging nucleotides by, for example, activity of certain types of DNA polymerase such as Taq polymerase or Klenow exo minus polymerase which has a non-template-dependent terminal transferase activity that adds a single deoxynucleotide, for example, deoxyadenosine (A) to the 3' ends of a DNA molecule, for example, a PCR product. Such enzymes can be used to add a single nucleotide 'A' to the blunt ended 3' terminus of each strand of the double-stranded target fragments. Thus, an 'A' could be added to the 3' terminus of each end repaired strand of the double-stranded target fragments by reaction with Taq or Klenow exo minus polymerase, while the universal adapter polynucleotide construct could be a T-construct with a compatible 'T' overhang present on the 3' terminus of each region of double stranded nucleic acid of the universal adapter. This end modification also prevents self-ligation of both vector and target such that there is a bias towards formation of the combined ligated adaptor-target-adaptor molecules.

Universal Adapters

The method includes attaching a universal adapter to each end of the double-stranded target fragments isolated from a source to result in adapter-target-adapter molecules. The attachment can be through standard library preparation techniques using ligation, or through tagmentation using transposase complexes (Gunderson et al., WO 2016/130704).

In one embodiment, the double-stranded target fragments of each specific fragmented sample are treated by first ligating identical universal adaptor molecules ('mismatched adaptors', the general features of which are defined below, and further described in copending application Gormley et al., U.S. Pat. No. 7,741,463, and Bignell et al., U.S. Pat. No. 8,053,192) to the 5' and 3' ends of the double-stranded target fragments (which may be of known, partially known or unknown sequence) to form adapter-target-adapter molecules. In one embodiment, the universal adaptor includes all sequences necessary for immobilizing the adapter-target-adapter molecules on an array for subsequent sequencing. In another embodiment, a PCR step is used to further modify the universal adapter present in each adapter-target-adapter molecule prior to immobilizing and sequencing. For instance, an initial primer extension reaction is carried out using a universal primer binding site in which extension products complementary to both strands of each individual adapter-target-adapter molecule are formed and add a universal extension primer site. The resulting primer extension products, and optionally amplified copies thereof, collectively provide a library of template polynucleotides that can be immobilized and then sequenced. The terms universal primer binding site and universal extension primer site are described in detail herein. The term library refers to the collection of target fragments containing known common sequences at their 3' and 5' ends, and may also be referred to as a 3' and 5' modified library.

The universal adapter polynucleotides used in the method of the disclosure are referred to herein as 'mismatched' adaptors because, as will be explained in detail herein, the adaptors include a region of sequence mismatch, i.e., they are not formed by annealing of fully complementary polynucleotide strands.

Mismatched adaptors for use herein are formed by annealing of two partially complementary polynucleotide strands so as to provide, when the two strands are annealed, at least one double-stranded region, also referred to as a region of double stranded nucleic acid, and at least one unmatched single-stranded region, also referred to as a region of single-stranded non-complementary nucleic acid strands.

The 'double-stranded region' of the universal adapter is a short double-stranded region, typically including 5 or more consecutive base pairs, formed by annealing of the two partially complementary polynucleotide strands. This term refers to a double-stranded region of nucleic acid in which the two strands are annealed and does not imply any particular structural conformation. As used herein, the term "double stranded," when used in reference to a nucleic acid molecule, means that substantially all of the nucleotides in the nucleic acid molecule are hydrogen bonded to a complementary nucleotide. A partially double stranded nucleic acid can have at least 10%, 25%, 50%, 60%, 70%, 80%, 90% or 95% of its nucleotides hydrogen bonded to a complementary nucleotide.

Generally it is advantageous for the double-stranded region to be as short as possible without loss of function. In this context, 'function' refers to the ability of the double-stranded region to form a stable duplex under standard reaction conditions for an enzyme-catalyzed nucleic acid ligation reaction, which will be well known to the skilled reader (e.g. incubation at a temperature in the range of 4° C. to 25° C. in a ligation buffer appropriate for the enzyme), such that the two strands forming the universal adapter remain partially annealed during ligation of the universal adapter to a target molecule. It is not absolutely necessary for the double-stranded region to be stable under the conditions typically used in the annealing steps of primer extension or PCR reactions.

Because identical universal adapters are ligated to both ends of each target molecule, the target sequence in each adaptor-target-adaptor molecule will be flanked by complementary sequences derived from the double-stranded region of the universal adapters. The longer the double-stranded region, and hence the complementary sequences derived therefrom in the adaptor-target-adaptor constructs, the greater the possibility that the adaptor-target-adaptor construct is able to fold back and base-pair to itself in these regions of internal self-complementarity under the annealing conditions used in primer extension and/or PCR. It is, therefore, generally preferred for the double-stranded region to be 20 or less, 15 or less, or 10 or less base pairs in length in order to reduce this effect. The stability of the double-stranded region may be increased, and hence its length potentially reduced, by the inclusion of non-natural nucleotides which exhibit stronger base-pairing than standard Watson-Crick base pairs.

In one embodiment, the two strands of the universal adapter are 100% complementary in the double-stranded region. It will be appreciated that one or more nucleotide mismatches may be tolerated within the double-stranded region, provided that the two strands are capable of forming a stable duplex under standard ligation conditions.

Universal adaptors for use herein will generally include a double-stranded region forming the 'ligatable' end of the adaptor, i.e. the end that is joined to a double-stranded target fragment in the ligation reaction. The ligatable end of the universal adaptor may be blunt or, in other embodiments, short 5' or 3' overhangs of one or more nucleotides may be present to facilitate/promote ligation. The 5' terminal nucleotide at the ligatable end of the universal adapter is typically phosphorylated to enable phosphodiester linkage to a 3' hydroxyl group on the target polynucleotide.

The term 'unmatched region' refers to a region of the universal adaptor, the region of single-stranded non-complementary nucleic acid strands, wherein the sequences of the two polynucleotide strands forming the universal adaptor exhibit a degree of non-complementarity such that the two strands are not capable of fully annealing to each other under standard annealing conditions for a primer extension or PCR reaction. The unmatched region(s) may exhibit some degree of annealing under standard reaction conditions for an enzyme-catalyzed ligation reaction, provided that the two strands revert to single stranded form under annealing conditions in an amplification reaction.

The region of single-stranded non-complementary nucleic acid strands includes at least one universal primer binding site. A universal primer binding site is a universal sequence that can be used for amplification and/or sequencing of a target fragment ligated to the universal adapter.

The region of single-stranded non-complementary nucleic acid strands also includes at least one sample-specific tag. The method of the invention uses sample-specific tags as markers characteristic of the source of particular target fragments on an array. Generally the sample-specific tag is a synthetic sequence of nucleotides that is part of the universal adapter which is added to the target fragments as part of the template or library preparation step. Accordingly, a sample-specific tag is a nucleic acid sequence tag which is attached to each of the target molecules of a particular sample, the presence of which is indicative of, or is used to identify, the sample or source from which the target molecules were isolated.

Preferably the sample-specific tag may be up to 20 nucleotides in length, more preferably 1-10 nucleotides, and most preferably 4-6 nucleotides in length. A four nucleotide tag gives a possibility of multiplexing 256 samples on the same array, a six base tag enables 4096 samples to be processed on the same array.

The region of single-stranded non-complementary nucleic acid strands also includes at least one universal primer extension binding site. A universal primer extension binding site can be used to capture multiple different nucleic acids, e.g., multiple different adapter-target-adapter molecules using a population of universal capture nucleic acids that are complementary to the universal primer extension binding site. In one embodiment, the universal primer extension binding site is part of the universal adapter when it is ligated to the double-stranded target fragments, and in another embodiment the universal primer extension binding site is added to the universal adapter after the universal adapter is ligated to the double-stranded target fragments. The addition can be accomplished using routine methods, including PCR-based methods.

It is to be understood that the 'unmatched region' is provided by different portions of the same two polynucleotide strands which form the double-stranded region(s). Mismatches in the adaptor construct can take the form of one strand being longer than the other, such that there is a single stranded region on one of the strands, or a sequence selected such that the two strands do not hybridize, and thus form a single stranded region on both strands. The mismatches may also take the form of 'bubbles', wherein both ends of the universal adapter construct(s) are capable of hybridizing to each other and forming a duplex, but the central region is not. The portion of the strand(s) forming the unmatched region are not annealed under conditions in which other portions of the same two strands are annealed to form one or more double-stranded regions. For avoidance of doubt it is to be understood that a single-stranded or single base overhang at the 3' end of a polynucleotide duplex that subsequently undergoes ligation to the target sequences does not constitute an 'unmatched region' in the context of this disclosure.

The lower limit on the length of the unmatched region will typically be determined by function, for example, the need to provide a suitable sequence for i) binding of a primer for primer extension, PCR and/or sequencing (for instance, binding of a primer to a universal primer binding site), or for ii) binding of a universal capture nucleic acid for immobilization of a adapter-target-adapter to a surface (for instance, binding of a universal capture nucleic acid to a universal primer extension binding site). Theoretically there is no upper limit on the length of the unmatched region, except that in general it is advantageous to minimize the overall length of the universal adapter, for example, in order to facilitate separation of unbound universal adapters from adaptor-target-adaptor constructs following the ligation step. Therefore, it is generally preferred that the unmatched region should be less than 50, or less than 40, or less than 30, or less than 25 consecutive nucleotides in length.

The precise nucleotide sequence of the universal adapters is generally not material to the invention and may be selected by the user such that the desired sequence elements are ultimately included in the common sequences of the library of templates derived from the universal adapters, for example, to provide binding sites for particular sets of universal amplification primers and/or sequencing primers and/or universal capture nucleic acids. Additional sequence elements may be included, for example, to provide binding sites for sequencing primers which will ultimately be used in sequencing of template molecules in the library, or products derived from amplification of the template library, for example on a solid support.

Although the precise nucleotide sequence of the universal adapter is generally non-limiting to the disclosure, the sequences of the individual strands in the unmatched region should be such that neither individual strand exhibits any internal self-complementarity which could lead to self-annealing, formation of hairpin structures, etc. under standard annealing conditions. Self-annealing of a strand in the unmatched region is to be avoided as it may prevent or reduce specific binding of an amplification primer to this strand.

The mismatched adaptors are preferably formed from two strands of DNA, but may include mixtures of natural and non-natural nucleotides (e.g. one or more ribonucleotides) linked by a mixture of phosphodiester and non-phosphodiester backbone linkages. Other non-nucleotide modifications may be included such as, for example, biotin moieties, blocking groups and capture moieties for attachment to a solid surface, as discussed in further detail below.

The universal adaptors may contain exonuclease resistant modifications such as phosphorothioate linkages. Such modifications reduce the number of adaptor-dimers present in the library, because the two adaptors cannot undergo ligation without removal of their non-complementary overhangs. In one embodiment, the adaptors can be treated with an exonuclease enzyme prior to the ligation reaction with the target, to ensure that the overhanging ends of the strands cannot be removed during the ligation process. Treatment of the adaptors in this manner reduces the formation of the adaptor-dimers at the ligation step.

Ligation and Amplification

Ligation methods are known in the art and use standard methods. Such methods use ligase enzymes such as DNA ligase to effect or catalyze joining of the ends of the two polynucleotide strands of, in this case, the universal adapter and the double-stranded target fragments, such that covalent linkages are formed. The universal adapter may contain a 5'-phosphate moiety in order to facilitate ligation to the 3'-OH present on the target fragment. The double-stranded target fragment contains a 5'-phosphate moiety, either residual from the shearing process, or added using an enzymatic treatment step, and has been end repaired, and optionally extended by an overhanging base or bases, to give a 3'-OH suitable for ligation. In this context, joining means covalent linkage of polynucleotide strands which were not previously covalently linked. In a particular aspect of the disclosure, such joining takes place by formation of a phosphodiester linkage between the two polynucleotide strands, but other means of covalent linkage (e.g. non-phosphodiester backbone linkages) may be used.

As discussed herein, in one embodiment, universal adaptors used in the ligation are complete and include a universal primer binding site, a sample-specific tag sequence, and a universal extension primer binding site. The resulting plurality of adapter-target-adapter molecules can be used to prepare immobilized samples for sequencing.

Also as discussed herein, in one embodiment, universal adaptors used in the ligation include a universal primer binding site and a sample-specific tag sequence, and do not include a universal extension primer binding site. The resulting plurality of adapter-target-adapter molecules can be further modified to include specific sequences, such as a universal extension primer binding site. Methods for addition of specific sequences, such as a universal extension primer binding site, to universal primers that are ligated to double-stranded target fragments include PCR based methods, and are known in the art and are described in, for instance, Bignell et al. (U.S. Pat. No. 8,053,192) and Gunderson et al. (WO2016/130704).

In those embodiments where a universal adapter is modified, an amplification reaction is prepared. The contents of an amplification reaction are known by one skilled in the art and include appropriate substrates (such as dNTPs), enzymes (e.g. a DNA polymerase) and buffer components required for an amplification reaction. Generally amplification reactions require at least two amplification primers, often denoted 'forward' and 'reverse' primers (primer oligonucleotides) that are capable of annealing specifically to a part of the polynucleotide sequence to be amplified under conditions encountered in the primer annealing step of each cycle of an amplification reaction. In certain embodiments the forward and reverse primers may be identical. Thus the primer oligonucleotides must include an 'adaptor-target specific portion', being a sequence of nucleotides capable of annealing to a part of, that is, a primer-binding sequence, in the polynucleotide molecule to be amplified (or the complement thereof if the template is viewed as a single strand) during the annealing step.

Depending on the embodiment of the invention, the amplification primers may be universal for all samples, or one of the forward or reverse primers may carry the tag sequence that codes for the sample source. The amplification primers may hybridize across the tag region of the ligated adaptor, in which case unique primers will be needed for each sample nucleic acid. The amplification reaction may be performed with more than two amplification primers. In order to prevent the amplification of ligated adapter-adapter dimers, the amplification primers can be modified to contain nucleotides that hybridize across the whole of the ligated adapter and into the ligated template (or the dNTP's attached to the 3' end thereof). This first amplification primer can be modified and treated to help prevent exonuclease digestion of the strands, and thus it may be advantageous to have a first amplification primer that is universal and can amplify all samples rather than modifying and treating each of the tagged primers separately. The tagged primer can be introduced as a sample specific third primer in the amplification reaction, but does not need to be specially modified and treated to reduce exonuclease digestion. In the case of this embodiment the third amplification primer that carries the tag needs to contain a sequence that is the same as at least a portion of the first amplification primer such that it can be used to amplify the duplex resulting from extension of the first amplification primer.

In the context of the present invention, the term 'polynucleotide molecule to be amplified' refers to the original or starting adaptor-target-adaptor moleculeadded to the amplification reaction. The ' adaptor-target specific portion' in the forward and reverse amplification primers refers to a sequence capable of annealing to the original or initial adaptor-target-adaptor present at the start of the amplification reaction and reference to the length of the 'adaptor-target specific portion' relates to the length of the sequence in the primer which anneals to the starting adaptor-target. It will be appreciated that if the primers contain any nucleotide sequence which does not anneal to the starting adaptor-target in the first amplification cycle then this sequence may be copied into the amplification products (assuming the primer does not contain a moiety which prevents read-through of the polymerase). Hence the amplified template strands produced in the first and subsequent cycles of amplification may be longer than the starting adaptor-target strands.

Because the mismatched adapters can be different lengths, the length of adapter sequence added to the 3' and 5' ends of each strand may be different. The amplification primers may also be of different lengths to each other, and may hybridize to different lengths of the adapter, and therefore the length added to the ends of each strand can be controlled. In the case of nested PCR, the three or more amplification primers can be designed to be longer than the primer used to amplify the previous amplicon, so the length of the added nucleotides is fully controllable and may be hundreds of base pairs if desired. In one embodiment, the first amplification primer adds 13 bases to the ligated adapter, and the third amplification primer adds a further 27 bases such that one end of the amplicon is 40 bases longer than the short arm of adapter-target construct. The short arm of the adapter is 20 bases in length, meaning that the prepared template comprises the genomic region plus 60 added bases at the end. The second amplification primer is 25 bases longer than the long arm of adapter, which is 32 bases in length plus the additional T that hybridises across the DATP nucleoside added to the genomic sample. Thus the prepared template comprises the genomic fragment, plus the added DATP, plus 57 known bases. Thus in full, one strand of each template duplex comprises from the 5' end: 60 known bases, T, the genomic fragment, A, 57 known bases-3' end. This strand is fully complementary to a sequence: 5'-57 known bases, T, genomic fragment, A, 60 known bases-3' end. The length 57 and 6 are arbitrary, and shown for the purpose of clarification, and should not be viewed as limiting. The length of the added sequences may be 20-100 bases or more depending on the desired experimental design.

The forward and reverse primers may be of sufficient length to hybridize to the whole of the adaptor sequence and at least one base of the target sequence (or the nucleotide DNTP added as a 3'-overhang on the target strands). The forward and reverse primers may also contain a region that extends beyond the adaptor construct, and therefore the amplification primers may be at least 20-100 bases in length. The forward and reverse primers may be of significantly different lengths; for example one may be 20-40 bases, whereas the other one may be 40-100 bases in length. The nucleotide sequences of the adaptor-target specific portions of the forward and reverse primers are selected to achieve specific hybridisation to the adaptor-target sequences to be amplified under the conditions of the annealing steps of the amplification reaction, whilst minimizing non-specific hybridisation to any other target sequences present.

Skilled readers will appreciate that it is not strictly required for the adaptor-target specific portion to be 100% complementary, a satisfactory level of specific annealing can be achieved with less than perfectly complementary sequences. In particular, one or two mismatches in the adaptor-target specific portion can usually be tolerated without adversely affecting specificity for the template. Therefore the term ' adaptor-target specific portion' should not be interpreted as requiring 100% complementarity with the adaptor-target. However, the requirement that the primers do not anneal non-specifically to regions of the adaptor-target other than their respective primer-binding sequences must be fulfilled.

Amplification primers are generally single stranded polynucleotide structures. They may also contain a mixture of natural and non-natural bases and also natural and non-natural backbone linkages, provided that any non-natural modifications do not preclude function as a primer—that being defined as the ability to anneal to a template polynucleotide strand during conditions of the amplification reaction and to act as an initiation point for synthesis of a new polynucleotide strand complementary to the template strand.

Primers may additionally comprise non-nucleotide chemical modifications, for example phosphorothioates to increase exonuclease resistance, again provided such that modifications do not prevent primer function. Modifications may, for example, facilitate attachment of the primer to a solid support, for example a biotin moiety. Certain modifications may themselves improve the function of the molecule as a primer, or may provide some other useful functionality, such as providing a site for cleavage to enable the primer (or an extended polynucleotide strand derived therefrom) to be cleaved from a solid support.

In an embodiment wherein tags are attached to the adaptors, the amplification can be carried out on either the pooled or unpooled samples. In an embodiment wherein universal adaptors are used, tags are be part of the amplification primers, and therefore, each sample is amplified independently prior to pooling. The pooled nucleic acid samples can then be processed for sequencing.

Removal of Undesirable Molecules

The combined ligated polynucleotide sequences (the adaptor-target-adaptor molecules), unligated universal adapter polynucleotide constructs, and/or incomplete products are exposed to conditions to reduce, or eliminate to an undetectable level, the amount of undesirable molecules, e.g., unligated universal adapter polynucleotide constructs and/or incomplete products. The methods for reducing undesirable molecules may be performed on each library separately or on pooled samples. In one embodiment, gel purification or solid phase reverse immobilization (SPRI) methods can be used. Gel purification and SPRI methods for separation of unligated DNA molecules such as the unligated universal adapter polynucleotide constructs described herein are known to the skilled person and are routine, and can be easily applied by the skilled person to removal of incomplete products.

In a preferred embodiment, undesirable molecules such as the unligated universal adapter polynucleotide constructs are removed by exonuclease. In one embodiment, exonucleases useful herein have a 5' to 3' DNA exonuclease activity, and optionally, an exonuclease is biased for double stranded DNA. In one embodiment, an exonuclease specifically targets the 5' end of a double stranded DNA, where the 5' end has a 5' phosphate. In another embodiment, an exonuclease specifically targets the 5' end of a double stranded DNA, where the 5' end does not have a 5' phosphate. Without intending to be limiting, use of exonucleases useful herein having a 5' to 3' DNA exonuclease activity is designed to remove at least one strand of unligated universal adaptors by digestion at the 5' end of the double stranded region of the universal adaptors.

In one embodiment, an exonuclease useful herein has a 5' to 3' DNA exonuclease activity that is biased for double stranded DNA having a 5' phosphate at the 5' end of the region of double stranded nucleic acid of a universal adapter. Examples of 5' to 3' exonucleases biased for dsDNA having a 5' phosphate at the 5' end of the region of double stranded nucleic acid include, but are not limited to, lambda exonuclease (New England Biolabs). The presence of the 5' phosphate at the 5' end of the double-stranded region biases an exonuclease such as lambda exonuclease for the 5' end of the double-stranded region of an unligated universal adapter. In one embodiment, the 5' end of the strand that is part of the region of single stranded non-complementary nucleic acid strands does not include a 5' phosphate. In one embodiment, the 5' end of the strand that is part of the single stranded region is modified to reduce the ability of the exonuclease to use it as a substrate.

In another embodiment, an exonuclease useful herein has both 5' to 3' and 3' to 5' DNA exonuclease activity. When such an exonuclease is biased for double stranded DNA but also uses single stranded DNA as a substrate, universal adapters used for ligation can include two types of modifications. One modification is at the 3' end of the single stranded region to block the 3' to 5' DNA exonuclease activity. This modification prevents digestion of adaptor-target-adaptor molecules from the free 3' ends. The second modification is at the 5' end of the strand that is part of the region of single stranded non-complementary nucleic acid strands. This modification prevents digestion of adaptor-target-adaptor molecules from the free 5' ends. Examples of modifications include, but are not limited to, inclusion of phosphorothioate linkages. Examples of exonucleases having a 5' to 3' DNA exonuclease activity and 3' to 5' DNA exonuclease activity, and biased for double stranded DNA, include but are not limited to exonuclease VIII truncated (New England Biolabs).

In a preferred embodiment, undesirable molecules such as incomplete products are removed by exonuclease. In one embodiment, exonucleases useful herein have a 3' to 5' DNA exonuclease activity, and optionally, an exonuclease is biased for double stranded DNA that is blunt ended or has a recessed 3' terminus. In one embodiment, an exonuclease having a 3' to 5' DNA exonuclease activity has reduced activity on single stranded DNA (e.g., it is biased for double stranded DNA) and/or reduced activity on a 3' extension when the single strand is 4 or more bases in length (e.g., it is biased for double stranded DNA that has a single stranded 3' extension of 3 bases or less). Without intending to be limiting, use of exonucleases useful herein having a 3' to 5' DNA exonuclease activity is designed to remove at least one strand of incomplete products by digestion at the 3' end of the double stranded region of the incomplete product. Examples of incomplete products include adaptor-target molecules, and target molecules that do not include an adaptor at either end. Examples of 3' to 5' exonucleases biased for double stranded DNA having blunt or recessed 3' termini include, but are not limited to, Exonuclease III (New England Biolabs).

During or following exonuclease treatment a number of compounds and compositions may result. For example, a compound or composition comprising a polynucleotide having an adapter-target-adapter sequence of nucleotides in which a 3' end of the polynucleotide is blocked for exonuclease activity may result. A library or a composition comprising a plurality of such 3' blocked polynucleotides may result. Pooled libraries and composition comprising pooled libraries of such polynucleotides may result. The compositions may further comprise universal adapters that are not attached to the target polynucleotides, and/or incomplete products.

By way of further example, a composition comprising a polynucleotide having an adapter-target-adapter sequence of nucleotides and an exonuclease may result. Similarly, a composition comprising a library polynucleotides and the exonuclease may result. Compositions comprising pooled libraries of such polynucleotides and the exonuclease may result. The compositions may further comprise universal adapters that are not attached to the target polynucleotides.

3' Blocking

In one embodiment, in addition to reducing or eliminating the amount of undesirable molecules, such as unligated adapters and/or incomplete products, the combined ligated polynucleotide sequences (the adaptor-target-adaptor molecules) and undesirable molecules, e.g., unligated universal adapter polynucleotides, are optionally 3' blocked, meaning that the polynucleotides are modified to prevent incorporation of nucleotides on the 3' end to extend the polynucleotide or the oligonucleotide from the 3' end. 3' blocking may be performed on each library separately or on pooled libraries.

The resulting composition may be subjected to a 3' blocking reaction to block the 3' ends of the polynucleotides or oligonucleotides in the sample, such as adapter-target-adapter polynucleotides or residual unligated universal adapters. Extension of an oligonucleotide or polynucleotide having "blocked" 3' end by the addition of additional nucleotides in a 5' to 3' direction is prevented due to the blocked 3' end.

3' blocking may be accomplished in any suitable manner. For example, a blocking moiety may be covalently attached to a 3' hydroxyl group at the 3' end to prevent extension from the 3' end.

In some embodiments, the 3'-OH blocking group may be removable, such that the 3' carbon atom has attached a group of the structure —O—Z, wherein Z is any of $—C(R')_2—O—R''$, $—C(R')_2—N(R'')_2$, $—C(R')_2—N(H)R''$, $—C(R')_2—S—R''$ and $—C(R')_2—F$, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; or $(R')_2$ represents an alkylidene group of formula $=C(R''')_2$ wherein each R''' may be the same or different and is selected from the group comprising hydrogen and halogen atoms and alkyl groups; and wherein said molecule may be reacted to yield an intermediate in which each R" is exchanged for H or, where Z is $—C(R')_2—F$, the F is exchanged for OH, SH or $NH_2$, preferably OH, which intermediate dissociates under aqueous conditions to afford a molecule with a free 3'OH; with the proviso that where Z is $—C(R')_2—S—R''$, both R' groups are not H. Where the blocking group is any of —C(R')$_2$—O—R", —C(R')$_2$—N(R")$_2$, —C(R')$_2$—N(H)R", —C(R')$_2$—S—R" and —C(R')$_2$—F, i.e. of formula Z, each R' may be independently H or an alkyl. Preferably, Z is of formula —C(R')$_2$—O—R", —C(R')$_2$—N(R")$_2$, —C(R')$_2$—N(H)R" and —C(R')$_2$—SR". Particularly preferably, Z is of the formula —C(R')$_2$—O—R", —C(R')$_2$—N(R")$_2$, and —C(R')$_2$—SR". R" may be a benzyl group or a substituted benzyl group. One example of groups of structure —O—Z wherein Z is —C(R')$_2$—N(R")$_2$ are those in which —N(R")$_2$ is azido (—$N_3$). One such example is azidomethyl wherein each R' is H. Alternatively, R' in Z groups of formula —C(R')$_2$—$N_3$ and other Z groups may be any of the other groups discussed herein. Examples of typical R' groups include $C_{1-6}$ alkyl, particularly methyl and ethyl. Other non-limiting examples of suitable 3' blocking groups are provided in Greene et al., "Protective Groups in Organic Synthesis," John Wiley & Sons, New York (1991), U.S. Pat. Nos. 5,990,300, 5,872,244, 6,232,465, 6,214,987, 5,808,045, 5,763,594, 7,057,026, 7,566,537, 7,785,796, 8,148,064, 8,394,586, 9,388,463, 9,410,200, 7,427,673, 7,772,384, 8,158,346, 9,121,062, 7,541,444, 7,771,973, 8,071,739, 8,597,881, 9,121,060, 9,388,464, 8,399,188, 8,808,988, 9,051,612, 9,469,873, and U.S. Pub. Nos. 2016/0002721 and 2016/0060692, the entire contents of which are incorporated herein by reference.

In some embodiments, the blocking group may remain covalently bound during subsequent processes associated with immobilizing adapter-target-adapter polynucleotides to a solid surface and sequencing.

In some embodiments, a dideoxynucleotide (ddNTP) is incorporated onto the 3' end of a polynucleotide to block the 3' end. The ddNTP may be incorporated in any suitable manner. In some embodiments, a ddNTP is incorporated via a terminal deoxynucleotidyl transferase (TdT). TdTs are able to incorporated nucleotides onto a 3' end of single or double stranded DNA without a template. In some embodiments, a ddNTP is incorporated onto a 3' end via a TdT in the presence of a DNA polymerase, such as, for example, Pol19, Pol812 or Pol963 polymerase. Non-limiting examples of other suitable polymerases are provided in U.S. Pat. Nos. 8,460,910, 8,852,910, 8,623,628, 9,273,352, 9,447,389, and U.S. Pub. Nos. 2015/0376582, 2016/0032377, 2016/0090579, 2016/0115461, the entire contents of which are incorporated herein by reference.

In some embodiments, a digoxigenin-labeled dideoxyuridine triphosphate is added to the 3' end using terminal transferase to block the 3' end. Kits for adding digoxigenin-labeled dideoxyuridine triphosphate to a 3' end of a polynucleotide are available from, for example, Sigma-Aldrich.

Any other suitable process may also be employed to modify the 3' ends of the polynucleotides.

During or following 3' blocking a number of compounds and compositions may result. For example, a compound or composition comprising a polynucleotide having an adapter-target-adapter sequence of nucleotides in which a 3' end of the polynucleotide is blocked may result. A library or a composition comprising a plurality of such 3' blocked polynucleotides may result. Pooled libraries and composition comprising pooled libraries of such polynucleotides may result. The compositions may further comprise universal adapters that are not attached to the target polynucleotides.

By way of further example, a composition comprising a polynucleotide having an adapter-target-adapter sequence of nucleotides and an enzyme and reagent for blocking 3' ends of the polynucleotide may result. Similarly, a composition comprising a library of polynucleotides and the enzyme and reagent may result. Compositions comprising pooled libraries of such polynucleotides and the enzyme and reagent may result. The compositions may further comprise adapter oligonucleotides that are not attached to the target polynucleotides. In some embodiments, the compositions comprise a ddNTP. The compositions may further comprise a DNA polymerase, such as, for example, Pol19, Pol812 or Pol963 polymerase.

Additional compositions may include a polynucleotide having an adapter-target-adapter sequence of nucleotides, an enzyme and reagent for blocking 3' ends of the polynucleotide, and an exonuclease. Similarly, a composition comprising a library of polynucleotides, the enzyme and reagent, and the exonuclease may result. Compositions comprising pooled libraries of such polynucleotides, the enzyme and reagent, and the exonuclease, may result. The compositions may further comprise adapter oligonucleotides that are not attached to the target polynucleotides. In some embodiments, the compositions comprise a ddNTP. The compositions may further comprise a DNA polymerase, such as, for example, Pol19, Pol812 or Pol963 polymerase.

Following blocking a clean-up step, such as described above, may be performed prior to immobilizing the polynucleotides on a solid surface for sequencing.

Methods for reducing or eliminating the amount of unligated universal adapter polynucleotide constructs, and methods for 3' blocking polynucleotides can be performed concurrently, or sequentially in any order.

If the libraries have not been pooled, they may be pooled prior to immobilizing on a surface of sequencing.

The exonuclease treatment described herein to reduce or eliminate unligated universal adaptors can be used immediately following the ligation, or can be used following the PCR based methods to add a universal extension primer binding site.

Preparation of Immobilized Samples for Sequencing

The plurality of adapter-target-adapter molecules from one or more sources are then immobilized and amplified prior to sequencing. Methods for attaching adapter-target-adapter molecules from one or more sources to a substrate are known in the art. Likewise, methods for amplifying immobilized adapter-target-adapter molecules include, but are not limited to, bridge amplification and kinetic exclusion. Methods for immobilizing and amplifying prior to sequencing are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

A sample, including pooled samples, can then be immobilized in preparation for sequencing. Sequencing can be performed as an array of single molecules, or can be amplified prior to sequencing. The amplification can be carried out using one or more immobilized primers. The immobilized primer(s) can be a lawn on a planar surface, or on a pool of beads. The pool of beads can be isolated into an emulsion with a single bead in each "compartment" of the emulsion. At a concentration of only one template per "compartment", only a single template is amplified on each bead.

The term "solid-phase amplification" as used herein refers to any nucleic acid amplification reaction carried out on or in association with a solid support such that all or a portion of the amplified products are immobilized on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilized on the solid support. Solid phase PCR covers systems such as emulsions, wherein one primer is anchored to a bead and the other is in free solution, and colony formation in solid phase gel matrices wherein one primer is anchored to the surface, and one is in free solution.

In some embodiments, the solid support comprises a patterned surface. A "patterned surface" refers to an arrangement of different regions in or on an exposed layer of a solid support. For example, one or more of the regions can be features where one or more amplification primers are present. The features can be separated by interstitial regions where amplification primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. Exemplary patterned surfaces that can be used in the methods and compositions set forth herein are described in U.S. Pat. Nos. 8,778,848, 8,778,849 and 9,079,148, and US Pub. No. 2014/0243224, each of which is incorporated herein by reference.

In some embodiments, the solid support comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface can be wells in an array of wells (e.g. microwells or nanowells) on glass, silicon, plastic or other suitable solid supports with patterned, covalently-linked gel such as poly(N-(5-azidoacetamidylpentyl) acrylamide-co-acrylamide) (PAZAM, see, for example, US Pub. No. 2013/184796, WO 2016/066586, and WO 2015/002813, each of which is incorporated herein by reference in its entirety). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However in many embodiments, the gel need not be covalently linked to the wells. For example, in some conditions silane free acrylamide (SFA, see, for example, U.S. Pat. No. 8,563,477, which is incorporated herein by reference in its entirety) which is not covalently attached to any part of the structured substrate, can be used as the gel material.

In particular embodiments, a structured substrate can be made by patterning a solid support material with wells (e.g. microwells or nanowells), coating the patterned support with a gel material (e.g. PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of target nucleic acids (e.g. a fragmented human genome) can then be contacted with the polished substrate such that individual target nucleic acids will seed individual wells via interactions with primers attached to the gel material; however, the target nucleic acids will not occupy the interstitial regions due to absence or inactivity of the gel material. Amplification of the target nucleic acids will be confined to the wells since absence or inactivity of gel in the interstitial regions prevents outward migration of the growing nucleic acid colony. The process is conveniently manufacturable, being scalable and utilizing conventional micro- or nano-fabrication methods.

Although the invention encompasses "solid-phase" amplification methods in which only one amplification primer is immobilized (the other primer usually being present in free solution), it is preferred for the solid support to be provided with both the forward and the reverse primers immobilized. In practice, there will be a 'plurality' of identical forward primers and/or a 'plurality' of identical reverse primers immobilized on the solid support, since the amplification process requires an excess of primers to sustain amplification. References herein to forward and reverse primers are to be interpreted accordingly as encompassing a 'plurality' of such primers unless the context indicates otherwise.

As will be appreciated by the skilled reader, any given amplification reaction requires at least one type of forward primer and at least one type of reverse primer specific for the template to be amplified. However, in certain embodiments the forward and reverse primers may comprise template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the invention. Other embodiments may use forward and reverse primers which contain identical template-specific sequences but which differ in some other structural features. For example one type of primer may contain a non-nucleotide modification which is not present in the other.

In all embodiments of the disclosure, primers for solid-phase amplification are preferably immobilized by single point covalent attachment to the solid support at or near the 5' end of the primer, leaving the template-specific portion of the primer free to anneal to its cognate template and the 3' hydroxyl group free for primer extension. Any suitable covalent attachment means known in the art may be used for this purpose. The chosen attachment chemistry will depend on the nature of the solid support, and any derivatization or functionalization applied to it. The primer itself may include a moiety, which may be a non-nucleotide chemical modification, to facilitate attachment. In a particular embodiment, the primer may include a sulphur-containing nucleophile, such as phosphorothioate or thiophosphate, at the 5' end. In the case of solid-supported polyacrylamide hydrogels, this nucleophile will bind to a bromoacetamide group present in the hydrogel. A more particular means of attaching primers and templates to a solid support is via 5' phosphorothioate attachment to a hydrogel comprised of polymerized acrylamide and N-(5-bromoacetamidylpentyl) acrylamide (BRAPA), as described fully in WO 05/065814.

Certain embodiments of the invention may make use of solid supports comprised of an inert substrate or matrix (e.g. glass slides, polymer beads, etc.) which has been "functionalized", for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel), but the intermediate material may itself be non-covalently attached to the substrate or matrix (e.g. the glass substrate). The term "covalent attachment to a solid support" is to be interpreted accordingly as encompassing this type of arrangement.

The pooled samples may be amplified on beads wherein each bead contains a forward and reverse amplification primer. In a particular embodiment, the library of templates prepared according to the first, second or third aspects of the invention is used to prepare clustered arrays of nucleic acid colonies, analogous to those described in U.S. Pub. No. 2005/0100900, U.S. Pat. No. 7,115,400, WO 00/18957 and WO 98/44151, the contents of which are incorporated herein by reference in their entirety, by solid-phase amplification and more particularly solid phase isothermal amplification. The terms 'cluster' and 'colony' are used interchangeably herein to refer to a discrete site on a solid support comprised of a plurality of identical immobilized nucleic acid strands and a plurality of identical immobilized complementary nucleic acid strands. The term "clustered array" refers to an array formed from such clusters or colonies. In this context the term "array" is not to be understood as requiring an ordered arrangement of clusters.

The term "solid phase", or "surface", is used to mean either a planar array wherein primers are attached to a flat surface, for example, glass, silica or plastic microscope slides or similar flow cell devices; beads, wherein either one or two primers are attached to the beads and the beads are amplified; or an array of beads on a surface after the beads have been amplified.

Clustered arrays can be prepared using either a process of thermocycling, as described in WO 98/44151, or a process whereby the temperature is maintained as a constant, and the cycles of extension and denaturing are performed using changes of reagents. Such isothermal amplification methods are described in patent application numbers WO 02/46456 and U.S. Pub. No. 2008/0009420, which are incorporated herein by reference in their entirety. Due to the lower temperatures required in the isothermal process, this is particularly preferred.

It will be appreciated that any of the amplification methodologies described herein or generally known in the art may be utilized with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354, which is incorporated herein by reference in its entirety. The above amplification methods may be employed to amplify one or more nucleic acids of interest. For example, PCR, including multiplex PCR, SDA, TMA, NASBA and the like may be utilized to amplify immobilized DNA fragments. In some embodiments, primers directed specifically to the polynucleotide of interest are included in the amplification reaction.

Other suitable methods for amplification of polynucleotides may include oligonucleotide extension and ligation, rolling circle amplification (RCA) (Lizardi et al., *Nat. Genet.* 19:225-232 (1998)) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835) technologies. It will be appreciated that these amplification methodologies may be designed to amplify immobilized DNA fragments. For example, in some embodiments, the amplification method may include ligation probe amplification or oligonucleotide ligation assay (OLA) reactions that contain primers directed specifically to the nucleic acid of interest. In some embodiments, the amplification method may include a primer extension-ligation reaction that contains primers directed specifically to the nucleic acid of interest. As a non-limiting example of primer extension and ligation primers that may be specifically designed to amplify a nucleic acid of interest, the amplification may include primers used for the GoldenGate assay (Illumina, Inc., San Diego, Calif.) as exemplified by U.S. Pat. Nos. 7,582,420 and 7,611,869.

Exemplary isothermal amplification methods that may be used in a method of the present disclosure include, but are not limited to, Multiple Displacement Amplification (MDA) as exemplified by, for example Dean et al., *Proc. Natl. Acad. Sci. USA* 99:5261-66 (2002) or isothermal strand displacement nucleic acid amplification exemplified by, for example U.S. Pat. No. 6,214,587. Other non-PCR-based methods that may be used in the present disclosure include, for example, strand displacement amplification (SDA) which is described in, for example Walker et al., *Molecular Methods for Virus Detection*, Academic Press, Inc., 1995; U.S. Pat. Nos. 5,455,166, and 5,130,238, and Walker et al., *Nucl. Acids Res.* 20:1691-96 (1992) or hyper-branched strand displacement amplification which is described in, for example Lage et al., *Genome Res.* 13:294-307 (2003). Isothermal amplification methods may be used with the strand-displacing Phi 29 polymerase or Bst DNA polymerase large fragment, 5'->3' exo- for random primer amplification of genomic DNA. The use of these polymerases takes advantage of their high processivity and strand displacing activity. High processivity allows the polymerases to produce fragments that are 10-20 kb in length. As set forth above, smaller fragments may be produced under isothermal conditions using polymerases having low processivity and strand-displacing activity such as Klenow polymerase. Additional description of amplification reactions, conditions and components are set forth in detail in the disclosure of U.S. Pat. No. 7,670,810, which is incorporated herein by reference in its entirety.

Another polynucleotide amplification method that is useful in the present disclosure is Tagged PCR which uses a population of two-domain primers having a constant 5' region followed by a random 3' region as described, for example, in Grothues et al. *Nucleic Acids Res.* 21(5):1321-2 (1993). The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers may be removed and further replication may take place using primers complementary to the constant 5' region.

In some embodiments, isothermal amplification can be performed using kinetic exclusion amplification (KEA), also referred to as exclusion amplification (ExAmp). A nucleic acid library of the present disclosure can be made using a method that includes a step of reacting an amplification reagent to produce a plurality of amplification sites that each includes a substantially clonal population of amplicons from an individual target nucleic acid that has seeded the site. In some embodiments the amplification reaction proceeds until a sufficient number of amplicons are generated to fill the capacity of the respective amplification site. Filling an already seeded site to capacity in this way inhibits target nucleic acids from landing and amplifying at the site thereby producing a clonal population of amplicons at the site. In some embodiments, apparent clonality can be achieved even if an amplification site is not filled to capacity prior to a second target nucleic acid arriving at the site. Under some conditions, amplification of a first target nucleic acid can proceed to a point that a sufficient number of copies are made to effectively outcompete or overwhelm production of copies from a second target nucleic acid that is transported to the site. For example in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

Amplification sites in an array can be, but need not be, entirely clonal in particular embodiments. Rather, for some applications, an individual amplification site can be predominantly populated with amplicons from a first target nucleic acid and can also have a low level of contaminating amplicons from a second target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons. It will be understood that in an array or other collection of sites, at least 50%, 75%, 80%, 85%, 90%, 95% or 99% or more of the sites can be clonal or apparently clonal.

In some embodiments, kinetic exclusion can occur when a process occurs at a sufficiently rapid rate to effectively exclude another event or process from occurring. Take for example the making of a nucleic acid array where sites of the array are randomly seeded with target nucleic acids from a solution and copies of the target nucleic acid are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of US Application Pub. No. 2013/0338042, which is incorporated herein by reference in its entirety.

Kinetic exclusion can exploit a relatively slow rate for initiating amplification (e.g. a slow rate of making a first copy of a target nucleic acid) vs. a relatively rapid rate for making subsequent copies of the target nucleic acid (or of the first copy of the target nucleic acid). In the example of the previous paragraph, kinetic exclusion occurs due to the relatively slow rate of target nucleic acid seeding (e.g. relatively slow diffusion or transport) vs. the relatively rapid rate at which amplification occurs to fill the site with copies of the nucleic acid seed. In another exemplary embodiment, kinetic exclusion can occur due to a delay in the formation of a first copy of a target nucleic acid that has seeded a site (e.g. delayed or slow activation) vs. the relatively rapid rate at which subsequent copies are made to fill the site. In this example, an individual site may have been seeded with several different target nucleic acids (e.g. several target nucleic acids can be present at each site prior to amplification). However, first copy formation for any given target nucleic acid can be activated randomly such that the average rate of first copy formation is relatively slow compared to the rate at which subsequent copies are generated. In this case, although an individual site may have been seeded with several different target nucleic acids, kinetic exclusion will allow only one of those target nucleic acids to be amplified. More specifically, once a first target nucleic acid has been activated for amplification, the site will rapidly fill to capacity with its copies, thereby preventing copies of a second target nucleic acid from being made at the site.

An amplification reagent can include further components that facilitate amplicon formation and in some cases increase the rate of amplicon formation. An example is a recombinase. Recombinase can facilitate amplicon formation by allowing repeated invasion/extension. More specifically, recombinase can facilitate invasion of a target nucleic acid by the polymerase and extension of a primer by the polymerase using the target nucleic acid as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. No. 5,223,414 and U.S. Pat. No. 7,399,590, each of which is incorporated herein by reference.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, Mass.). Further, examples of useful formulations that include a helicase protein are described in U.S. Pat. No. 7,399,590 and U.S. Pat. No. 7,829,284, each of which is incorporated herein by reference.

Yet another example of a component that can be included in an amplification reagent to facilitate amplicon formation and in some cases increase the rate of amplicon formation is an origin binding protein.

Use in Sequencing/Methods of Sequencing

Following attachment of adaptor-target-adaptor molecules to a surface, the sequence of the immobilized and amplified adapter-target-adapter molecules is determined. Sequencing can be carried out using any suitable sequencing technique, and methods for determining the sequence of immobilized and amplified adapter-target-adapter molecules, including strand re-synthesis, are known in the art and are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." *Analytical Biochemistry* 242(1), 84-9; Ronaghi, M. (2001) "Pyrosequencing sheds light on DNA sequencing." *Genome Res.* 11(1), 3-11; Ronaghi, M., Uhlen, M. and Nyren, P. (1998) "A sequencing method based on real-time pyrophosphate." *Science* 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurase, and the level of ATP generated is detected via luciferase-produced photons. The nucleic acids to be sequenced can be attached to features in an array and the array can be imaged to capture the chemiluminescent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type.

Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluorophores can include fluorophores linked to the ribose moiety via a 3' ester linkage (Metzker, *Genome Res.* 15:1767-1776 (2005), which is incorporated herein by reference). Other approaches have separated the terminator chemistry from the cleavage of the fluorescence label (Ruparel et al., *Proc Natl Acad Sci USA* 102: 5932-7 (2005), which is incorporated herein by reference in its entirety). Ruparel et al. described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluorophore and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Pub. Nos. 2007/0166705, 2006/0188901, 2006/0240439, 2006/0281109, 2012/0270305, and 2013/0260372, U.S. Pat. No. 7,057,026, PCT Publication No. WO 05/065814, U.S. Patent Application Publication No. 2005/0100900, and PCT Publication Nos. WO 06/064199 and WO 07/010,251, the disclosures of which are incorporated herein by reference in their entireties.

Some embodiments can utilize detection of four different nucleotides using fewer than four different labels. For example, SBS can be performed utilizing methods and systems described in the incorporated materials of U.S. Pub. No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." *Trends Biotechnol.* 18, 147-151 (2000); Deamer, D. and D. Branton, "Characterization of nucleic acids by nanopore analysis", *Acc. Chem. Res.* 35:817-825 (2002); Li, J., M. Gershow, D. Stein, E. Brandin, and J. A. Golovchenko, "DNA molecules and configurations in a solid-state nanopore microscope" *Nat. Mater.* 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." *Clin. Chem.* 53, 1996-2001 (2007); Healy, K. "Nanopore-based single-molecule DNA analysis." *Nanomed.* 2, 459-481 (2007); Cockroft, S. L., Chu, J., Amorin, M. & Ghadiri, M. R. "A single-molecule nanopore device detects DNA polymerase activity with single-nucleotide resolution." *J. Am. Chem. Soc.* 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414, both of which are incorporated herein by reference, or nucleotide incorporations can be detected with zero-mode waveguides as described, for example, in U.S. Pat. No. 7,315,019, which is incorporated herein by reference, and using fluorescent nucleotide analogs and engineered polymerases as described, for example, in U.S. Pat. No. 7,405,281 and U.S. Pub. No. 2008/0108082, both of which are incorporated herein by reference. The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." *Science* 299, 682-686 (2003); Lundquist, P. M. et al. "Parallel confocal detection of single molecules in real time." *Opt. Lett.* 33, 1026-1028 (2008); Korlach, J. et al. "Selective aluminum passivation for targeted immobilization of single DNA polymerase molecules in zero-mode waveguide nano structures." *Proc. Natl. Acad. Sci. USA* 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in U.S. Pub. Nos. 2009/0026082; 2009/0127589; 2010/0137143; and 2010/0282617, all of which are incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/$cm^2$, 100 features/$cm^2$, 500 features/$cm^2$, 1,000 features/$cm^2$, 5,000 features/$cm^2$, 10,000 features/$cm^2$, 50,000 features/$cm^2$, 100,000 features/$cm^2$, 1,000,000 features/$cm^2$, 5,000,000 features/$cm^2$, or higher.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in U.S. Pub. Nos. 2010/0111768 and 2012/0270305, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeg™ platform (Illumina, Inc., San Diego, Calif.) and devices described in U.S. Pub. No. 2012/0270305, which is incorporated herein by reference.

Referring now to FIG. 1, a schematic drawing is shown of an adapter 100 that may be used in accordance with various embodiments described herein. The depicted adapter 100 comprises a double-stranded region 110 and a non-complementary single-stranded region 120. The double-stranded region 110 may be attached to a double-stranded target polynucleotide. In the depicted embodiment, the 5' end of the strand in the double-stranded region 110 includes an optional 5' phosphate (indicated by "W"), which aids in both ligation of the adapter 100 to a double-stranded target polynucleotide and digestion by an exonuclease having 5' to 3' exonuclease activity that is biased for double stranded DNA that includes a terminal 5' phosphate. Optionally, the free 5' end of the strand of the single stranded portion 120 is modified to protect the end from exonuclease activity (indicated by "X"), for instance, the free 5' end of the strand of the single stranded portion 120 does not include a 5' phosphate. If the adapter 100 is not attached to a double stranded target fragment, the unincorporated adapter may be degraded by one or more exonuclease having 5' to 3' exonuclease activity that is biased for double stranded DNA. The strand having 140, 142, and 144 is selectively degraded, leaving the other strand and adapter-target-adapter molecules intact. The optional modification at the free 5' end of the strand of the single stranded portion 120 can aid in reducing residual activity the 5' to 3' exonuclease may have for single stranded DNA. If the adapter 100 is part of an incomplete product, e.g., one adapter 100 is attached to a double stranded target molecule, the incomplete product can be degraded by one or more exonuclease having 3' to 5' exonuclease activity that is biased for double stranded DNA having a blunt or recessed 3' terminus. The strand having 130, 132, and 134 is selectively degraded, leaving the other strand and adapter-target-adapter molecules intact.

Figure 2:
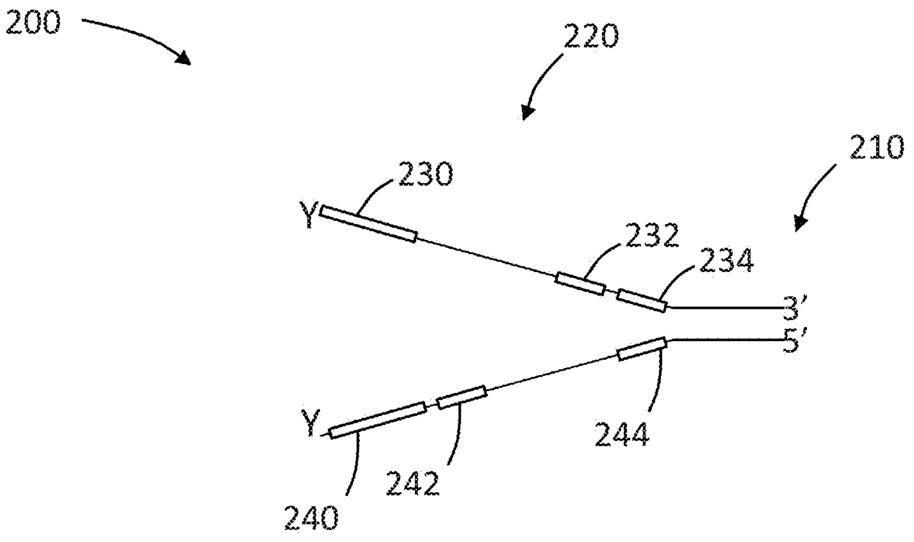

Referring now to FIG. 2, a schematic drawing is shown of an adapter 200 that may be used in accordance with various embodiments described herein. In the depicted embodiment the free ends of each strand of the single stranded portion 220 are modified (indicated by "Y") to protect the ends from exonuclease activity. If the adapter 100 is not attached to a double stranded target fragment, the unincorporated adapter may be digested by one or more exonuclease having both 5' to 3' exonuclease activity and 3' to 5' exonuclease activity. The protection of the two free ends of each strand of the single stranded portion 220 prevents the exonuclease from using desired adapter-target-adapter molecules as a substrate. If the adapter 200 is part of an incomplete product, e.g., one adapter 200 is attached to a double stranded target molecule, the incomplete product can be degraded by one or more exonuclease having 3' to 5' exonuclease activity that is biased for double stranded DNA having a blunt or recessed 3' terminus. The protection of the two free ends of each strand of the single stranded portion 220 prevents the exonuclease from using desired adapter-target-adapter molecules as a substrate.

Figure 3:
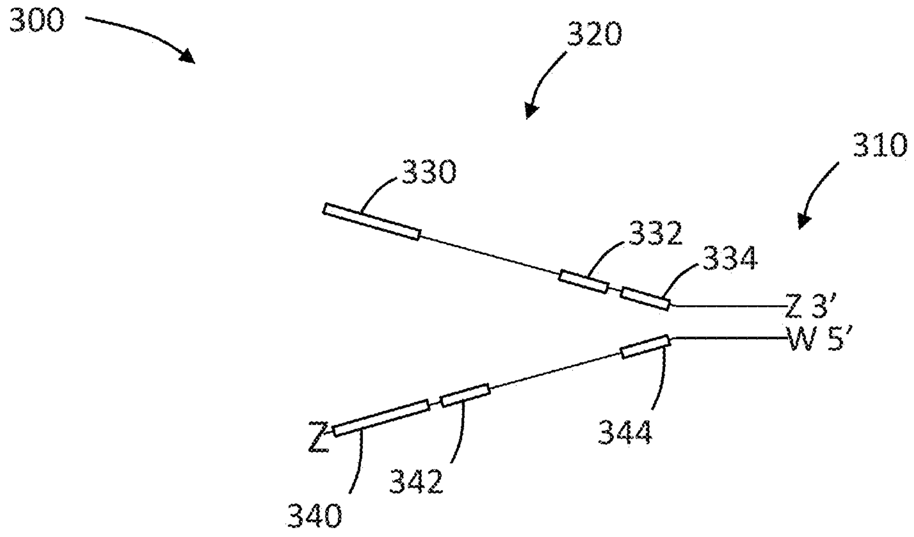

Referring now to FIG. 3, a schematic drawing is shown of an adapter 300 that may be used in accordance with various embodiments described herein. In the depicted embodiment, the 5' end of the strand in the double-stranded region 310 includes an optional 5' phosphate (indicated by "W"), which aids in both ligation of the adapter 300 to a double-stranded target polynucleotide and digestion by an exonuclease having 5' to 3' exonuclease activity that is biased for double stranded DNA that includes a terminal 5' phosphate. The double stranded region 310 may be attached to a double-stranded target polynucleotide if the 3' ends are not blocked. In the depicted embodiment, each strand of the adapter 300 comprises a blocked 3' end, indicated by the "Z." If the adapter 300 is not attached to a double stranded target fragment, the unincorporated adapter may be digested by one or more exonuclease having both 5' to 3' exonuclease activity and 3' to 5' exonuclease activity. Any remaining adapter sequences not degraded by the exonuclease cannot act as a primer for extension of any polynucleotide sequence during subsequent amplification and/or sequencing reactions.

Figure 4:
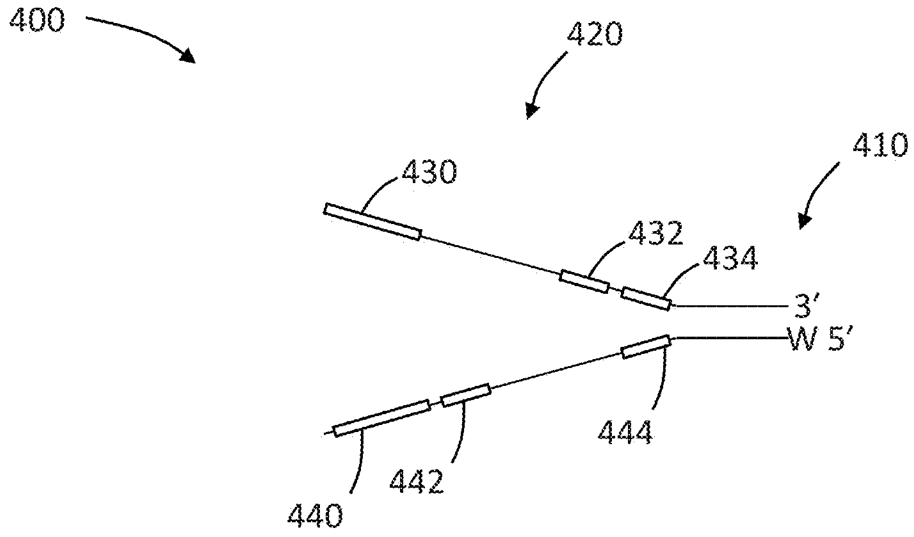

Referring now to FIG. 4, a schematic drawing is shown of an adapter 400 that may be used in accordance with various embodiments described herein. In the depicted embodiment, the 5' end of the strand in the double-stranded region 410 includes an optional 5' phosphate (indicated by "W"), which aids in both ligation of the adapter 400 to a double-stranded target polynucleotide. The double stranded region 410 may be attached to a double-stranded target polynucleotide. In those embodiments where one adapter is attached to a double-stranded target molecule (an incomplete product), the incomplete product may be digested by one or more exonuclease having 3' to 5' exonuclease activity that is biased for double stranded DNA having a blunt or recessed 3' terminus.

One depicted strand of the adapter 100 or 200 or 300 or 400 comprises a universal extension primer binding site 130 or 230 or 330 or 430 (e.g., P5), a tag sequence 132 or 232 or 332 or 432 (e.g., i5), and a sequencing primer binding site 134 or 234 or 334 or 434 (e.g., SBS3). The other depicted strand of the adapter 100 or 200 or 300 or 400 comprises a universal extension primer binding site 140 or 240 or 340 or 440 (e.g., P7'), a tag sequence 142 or 242 or 342 or 442 (e.g., i7), and a sequencing primer binding site 144 or 244 or 344 or 444 (e.g., SBS12').

The universal extension primer binding sites 130 or 230 or 330 or 430 (e.g., P5), 140 or 240 or 340 or 440 (e.g., P7') may hybridize to extension primer oligonucleotides attached to a solid surface for purposes of amplification or sequencing (if the adapter 100 or 200 or 300 or 400 was attached to a target polynucleotide). Universal extension primer binding site 140 or 240 or 340 or 440 (e.g., P7'), or a portion thereof, may also hybridize to a sequencing primer for sequencing index tag sequence 142 or 242 or 342 or 442 (e.g., i7). Alternatively the strand may comprise a further sequencing primer sequence (not shown).

Sequencing primer binding site 134 or 234 or 334 or 434 (e.g., SBS3) may hybridize to a sequencing primer to allow sequencing of index tag sequence 132 or 232 or 332 or 432 (e.g., i5). Tag sequence 142 or 242 or 342 or 442 and tag sequence 132 or 232 or 332 or 432 may be the same or different.

Sequencing primer binding site 144 or 244 or 344 or 444 (e.g., SBS12') may hybridize to a sequencing primer to allow sequencing of a target polynucleotide sequence (if attached to the adapter 100 or 200 or 300 or 400).

Sequencing primer binding sites 134 or 234 or 334 or 434 (e.g., SBS3), 144 or 244 or 344 or 444 (e.g., SBS12') may hybridize to, for example, PCR primers if the adapters are attached to a target in a multi-step process as described above.

It will be understood that a suitable adapter for use in various embodiments described herein may have more or less sequence features, or other sequence features, than those described regarding FIG. 1, FIG. 2, FIG. 3, and FIG. 4.

Figure 5:
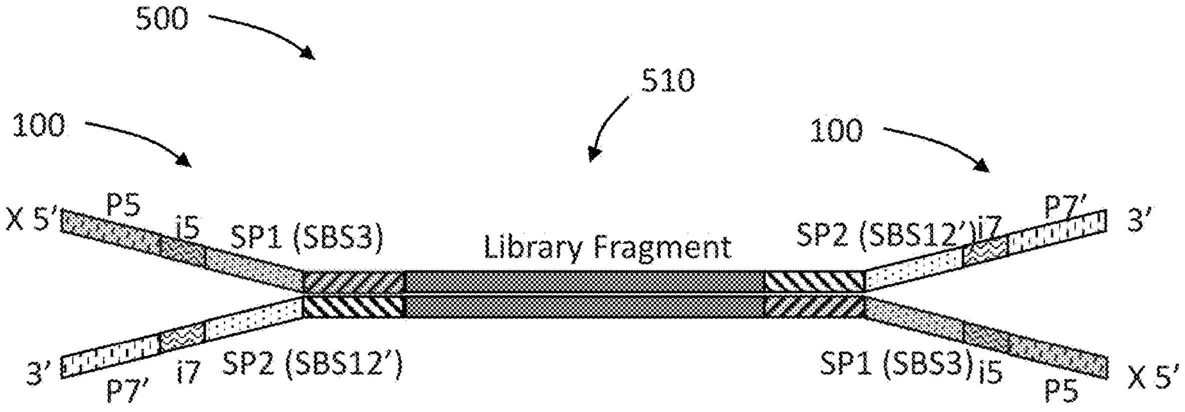
FIGS. 5, 6, 7, 8A and 8B are schematic drawings of multiple embodiments of a template polynucleotide having an adapter-target-adapter molecule (which may include an adapter, or a portion thereof) generally as shown in FIG. 1, 2, 3, or 4, respectively, according to various aspects of the disclosure presented herein.

Referring now to FIG. 5, a schematic drawing of an adapter-target-adapter 500 of a library having an adapter 100—template 510—adapter 100 sequence is shown. The adapter-target-adapter 510 is double stranded and attached to a double stranded portion of the adapters 100.

The 5' ends of the single stranded portions of the adapters are modified to protect from exonuclease digestion (indicated by "X"). Because the adapters 100 are ligated to both ends of the double stranded target fragment 510, no double stranded sequences are available on an adapter-target-adapter molecule for an exonuclease, thus the resulting adapter-target-adapter 400 is resistant to digestion by exonuclease.

Figure 6:
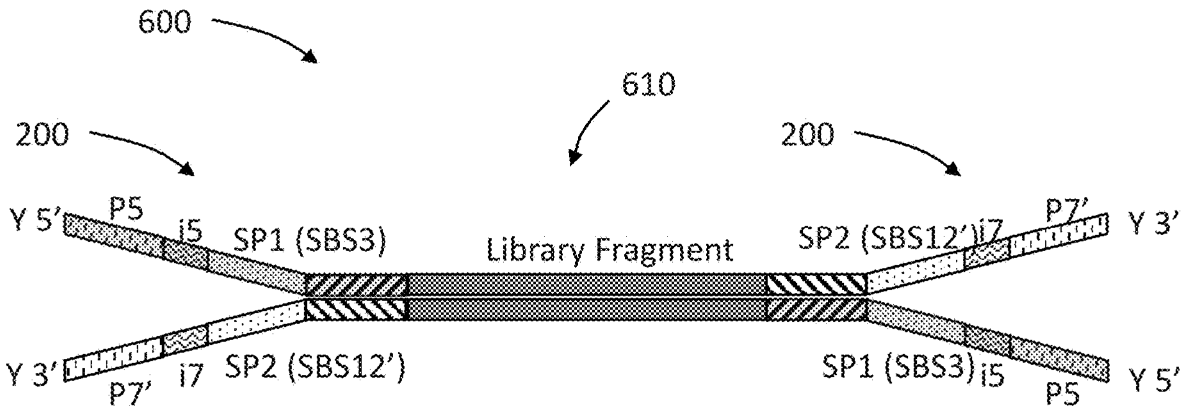

Referring now to FIG. 6, a schematic drawing of an adapter-target-adapter 600 of a library having an adapter 200—template 610—adapter 200 sequence is shown. The adapter-target-adapter 610 is double stranded and attached to a double stranded portion of the adapters 200. The ends of the single stranded portions of the adapters are modified to protect from exonuclease digestion (indicated by "Y").

Because the adapters 200 are ligated to both ends of the double stranded target fragment 610, no unblocked single stranded sequences are available on an adapter-target-adapter molecule for an exonuclease, thus the resulting adapter-target-adapter 600 is resistant to digestion by exonuclease.

Figure 7:
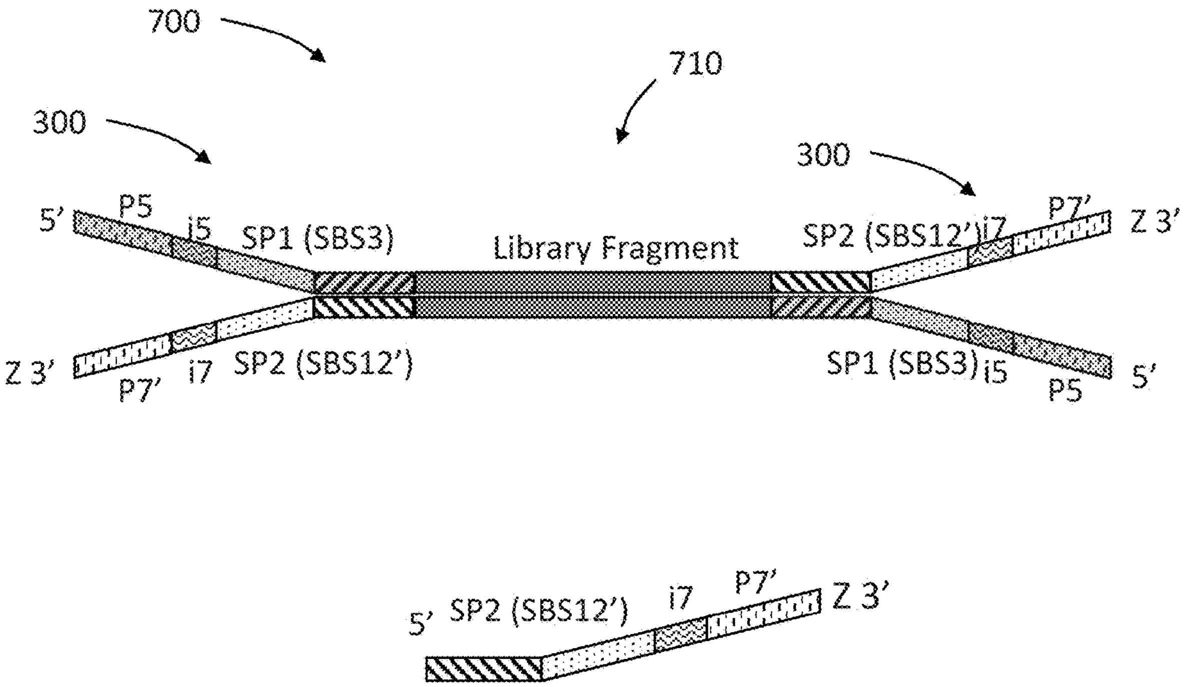

Referring now to FIG. 7, a schematic drawing of an adapter-target-adapter 700 of a library having an adapter 300—template 710—adapter 300 sequence is shown. The adapter-target-adapter 710 is double stranded and attached to a double stranded portion of the adapters 300. The ends of the single stranded regions of the adapters are modified to prevent them from acting as primers for extension of any polynucleotide in a flowcell. FIG. 7 further shows a schematic drawing of an adapter that was not completed degraded by exonuclease. A single strand of an adapter 300 is shown. This single stranded adapter cannot act as a primer for extension of any polynucleotide in a flowcell.

Figure 8A:
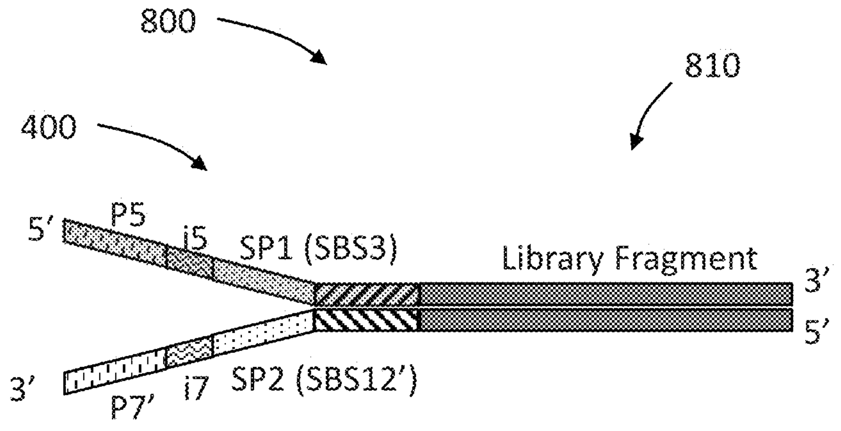
Figure 8B:
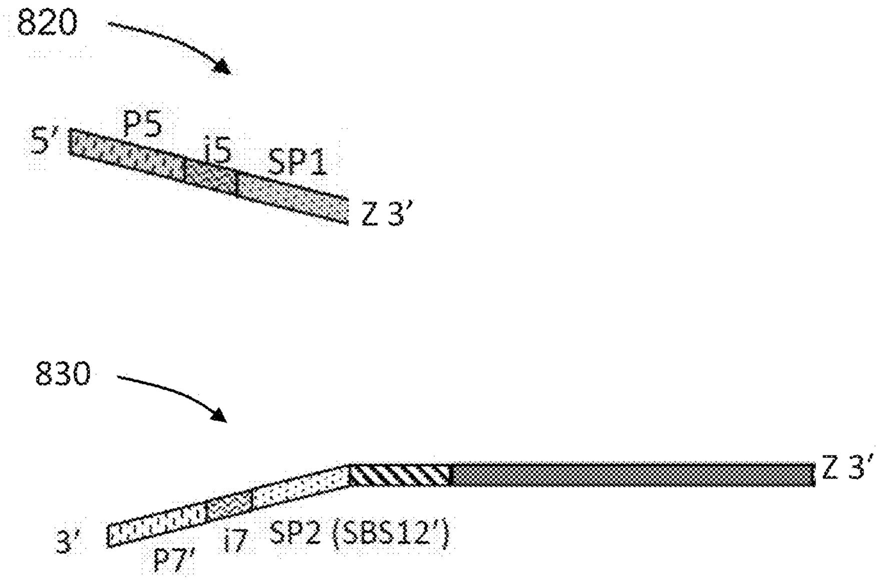

Referring now to FIG. 8A, a schematic drawing of an incomplete product of adapter-target 800 of a library having an adapter 400—template 810 sequence is shown. The adapter-target 800 is double stranded and attached to a double stranded portion of the adapter 400. FIG. 8B further shows a schematic drawing of one result of digestion of an incomplete product 800 with an exonuclease having 3' to 5' exonuclease activity that is biased for double stranded DNA having a blunt or recessed 3' terminus. Digestion of one strand of the double stranded portion of an adapter-target 800 from 3' to 5' may result in two single stranded molecules. One strand is a single strand adapter-target 830. The other adaptor strand 820 corresponds to one of the single stranded regions of an adapter 400. In this embodiment, the polynucleotides present in library pool are 3' blocked, as indicated by the "Z," after exposure to an exonuclease having 3' to 5' exonuclease activity that is biased for double stranded DNA having a blunt or recessed 3' terminus. These 3' blocked single stranded adapter-target 830 and adapter strand 820 cannot act as a primer for extension of any polynucleotide in a flowcell.

Figure 9A:
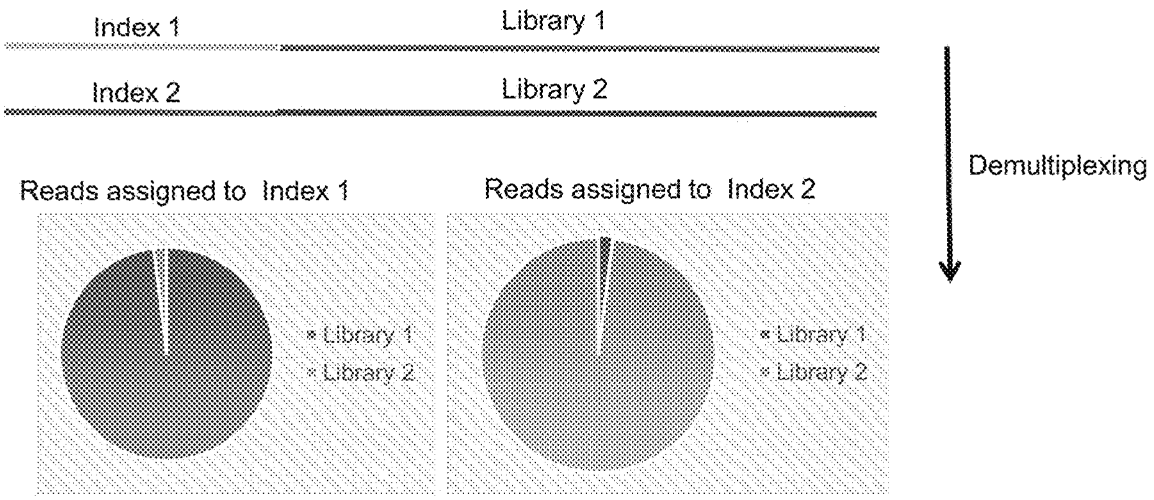
FIGS. 9A and 9B illustrate the nature of the index hopping phenomenon.
Figure 9B:
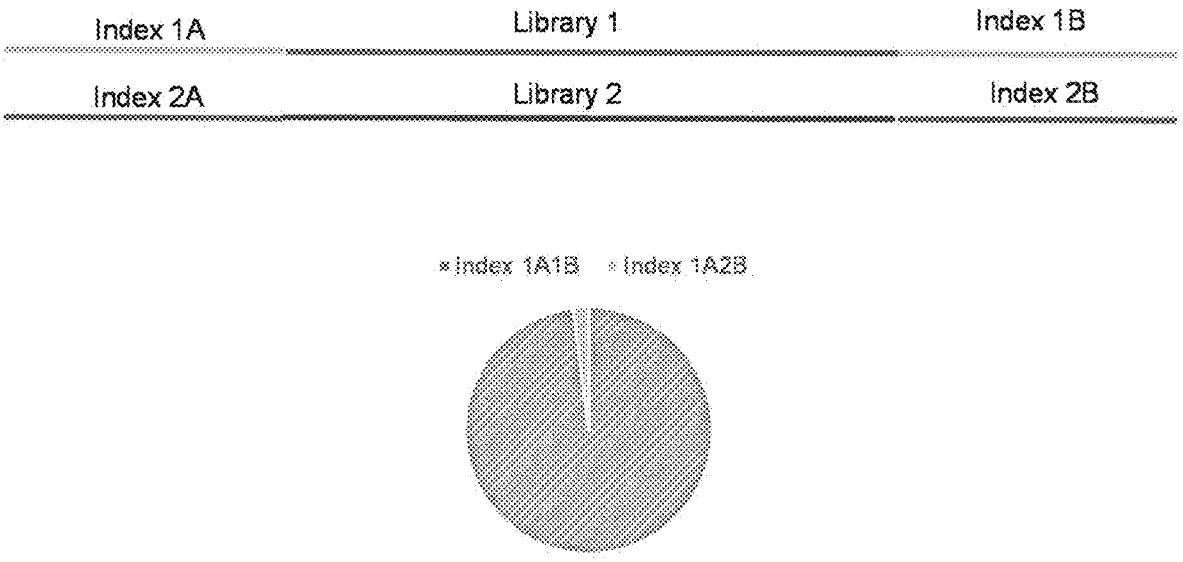

Referring now to FIGS. 9A and 9B, the nature of the index hopping phenomenon is illustrated. FIG. 9A shows how reads from a given sample are incorrectly demultiplexed and mixed with a different sample following demultiplexing. FIG. 9B demonstrates index hopping in a dual index system, where it leads to unexpected combinations of index tag sequences.

Referring now to FIGS. 10A and 10B, the general approach to measuring the rate of index hopping in a given system is illustrated. FIG. 10A shows an exemplary layout of a dual adapter plate, wherein each individual well of a 96-well plate contains a unique pair of index tag sequences (12 different P7 indices combined with 8 different P5 indices). FIG. 10B shows an experimental setup aimed at measuring the rate of index hopping, wherein 8 unique dual index tag combinations are used (i.e. no P5 index is expected to pair up with more than one P7 index and vice versa). Unexpected combinations of index tags (e.g., D505-D703) are then easily identified as instances of index hopping.

Figure 11A:
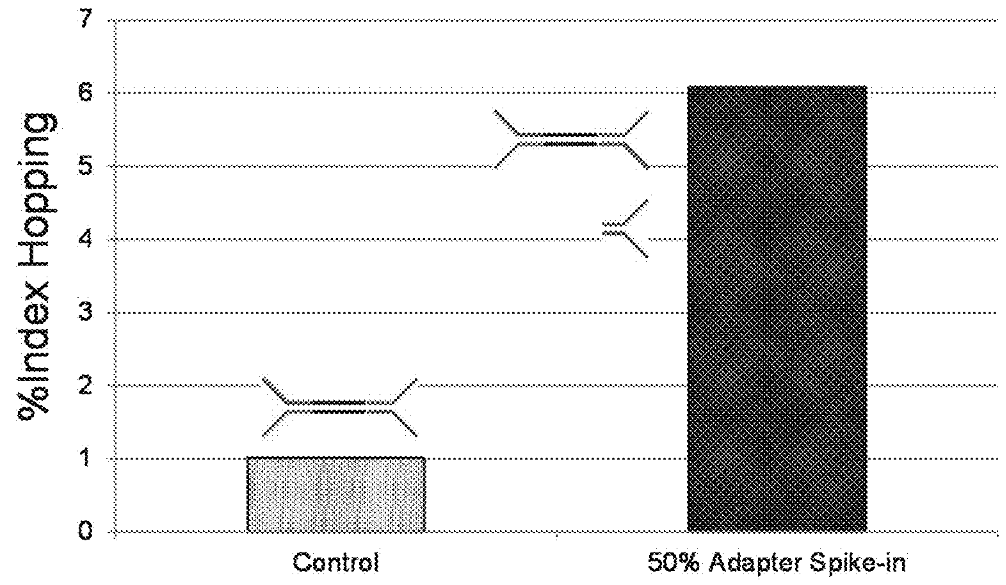
FIGS. 11A and 11B illustrate the effect of unligated adapters on the rate of index hopping.
Figure 11B:
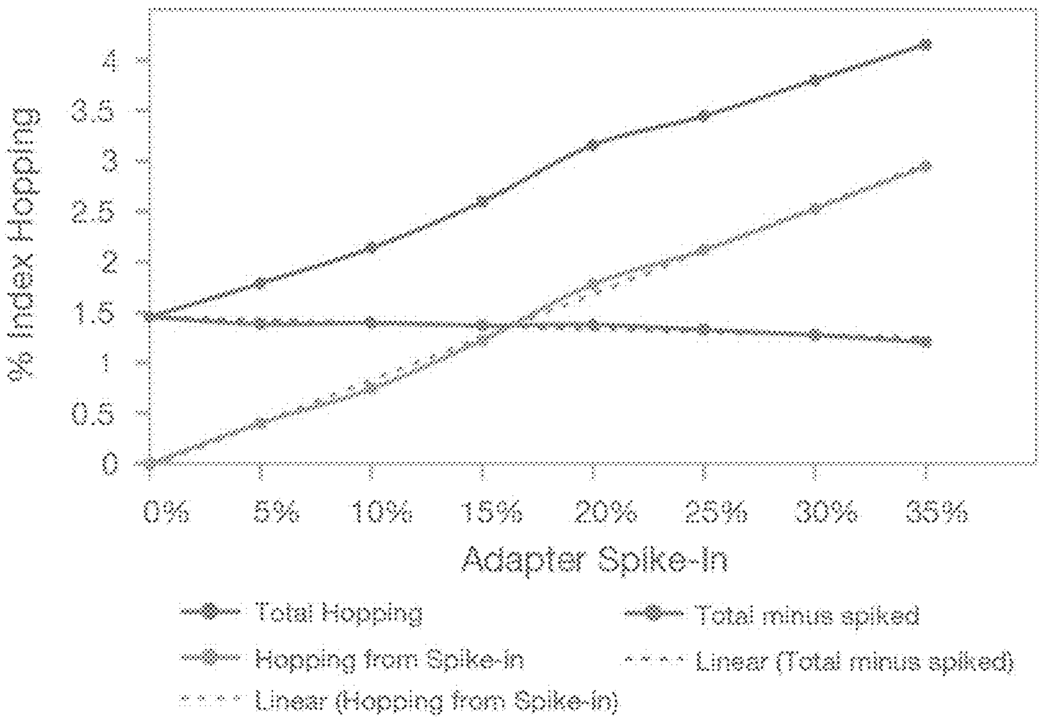

Referring not now to FIGS. 11A and 11B, the effect of unligated adapters on the rate of index hopping is illustrated. FIG. 11A shows a 6-fold increase in index hopping associated with a 50% spike-in of free adapters. FIG. 11B shows an approximately linear effect of the free forked adapter on the rate of index hopping within the range tested. The inventors also observed a more pronounced effect of free single-stranded P7 adapters on the rate of index hopping compared to free single-stranded P5 adapters (data not shown).

Figure 12A:
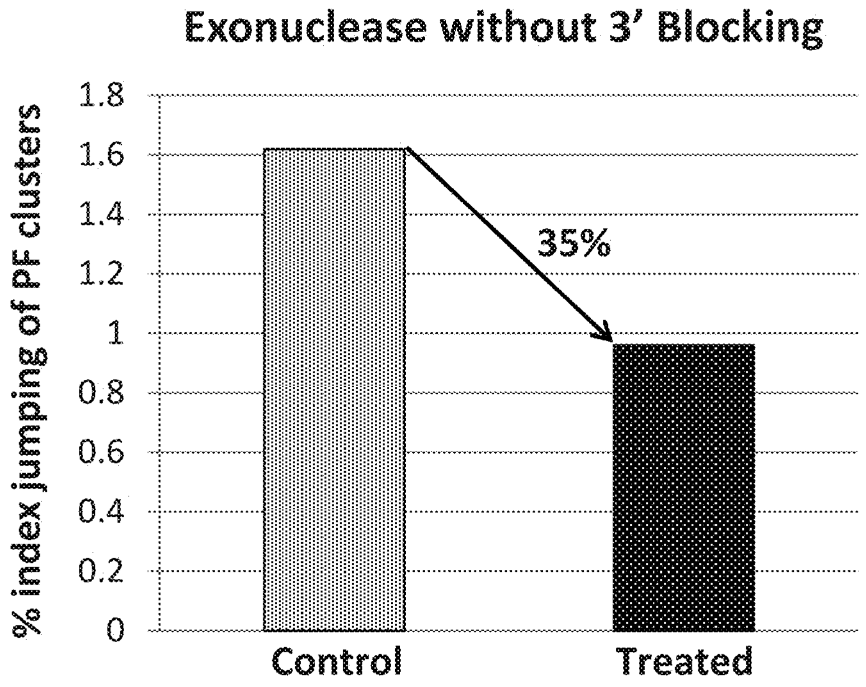
FIGS. 12A and 12B illustrate the effect of exonuclease treatment according to the present invention on the rates of index hopping in Illumina TruSeq® PCR-Free library preparation work flow, with (FIG. 12B) and without (FIG. 12A) 3' blocking.
Figure 12B:
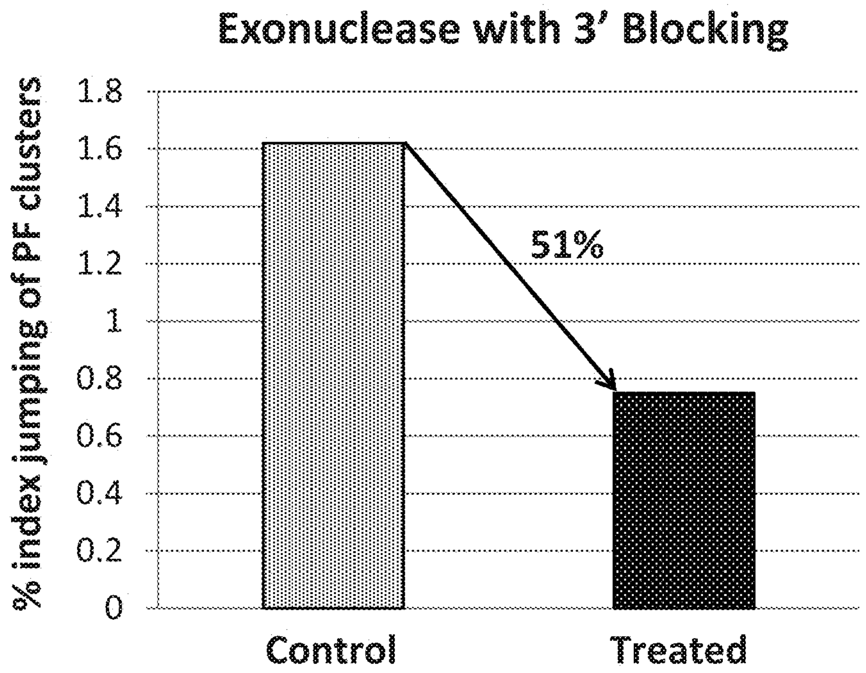

Referring now to FIGS. 12A and 12B, the effect of exonuclease treatment on the rates of index hopping in Illumina TruSeq® PCR-Free library preparation work flow, alone and in combination with 3' blocking, respectively, is illustrated. Significant decreases in index hopping were observed in both instances, though a stronger reduction was observed with the combined exonuclease and 3' blocking treatment.

The present invention is illustrated by the following examples. It is to be understood that the particular examples, materials, amounts, and procedures are to be interpreted broadly in accordance with the scope and spirit of the invention as set forth herein.

EXAMPLES

Example 1: Sample Protocol for Exonuclease Treatment with Optional 3' Blocking of Indexed Libraries This protocol explains how to perform an exonuclease treatment, either alone or combined with 3' blocking of DNA libraries, to reduce index hopping. This method is designed to be performed on DNA library pools prior to the denaturation step and subsequent cluster generation using the Illumina HiSeq® 4000 and similar sequencing platforms utilizing patterned flow cells and ExAmp based clustering (e.g., HiSeq® X and NovaSeq®).

Index hopping has been seen to occur where incorrect index sequences are assigned to the insert sequence resulting in sample misassignment. Performing this treatment on DNA sample pools before running on HiSeq® 4000 should reduce the index hopping levels by some level which cannot at this stage be predicted consistently.

Treatment workflow may be considered to involve four steps: (i) produce DNA sample pool; (ii) perform treatment, (iii) cleanup sample and quantify; and (iv) cluster and sequence sample pool.

Consumables/Equipment: Consumables and equipment may be supplied by a sequencing user or manufacture. User supplied consumables may include a DNA library sample pool—30 μl at concentration to be used for denaturation during clustering. The user may also supply freshly prepared 80% ethanol (EtOH).

Table 1 below illustrates some consumables and equipment that may be used.

TABLE 1

Consumables and Equipment

| Consumable/Equipment | Supplier |
|---|---|
| Ethanol 200 proof (absolute) for molecular biology | Sigma-Aldrich, Cat #E7023 |
| Magnetic stand-96 | Life Technologies, Cat #AM10027 |
| Vortexer | General lab supplier |
| 96-well thermal cycler (with heated lid) | General lab supplier |

A sequencing manufacturer may supply EMX (Exonuclease Mix), BMX (Blocking Mix), RSB (Resuspension Buffer), and SPB (Sample Purification Beads).

The EMX may include an exonuclease buffer (67 mM Glycine-KOH, 2.5 mM MgCl2, 50 μg/ml BSA) and Lambda Exonuclease (New England Biolabs, Cat #M0262S/L).

The BMX may include a sequencing premix (Tris buffer, sodium chloride, sucrose, magnesium sulfate, EDTA and Tween 20), a ddNTP mix, Pol19 DNA polymerase, and TDT terminal transferase.

The RSB may include a Tris buffer, pH 8.5.

The SPB may include AgenCourt® AMPure® XP beads (Beckman Coulter, Cat #A63880). The SPB should be vortexed before each use. The SPB should be vortexed frequently to make sure that beads are evenly distributed. The SPB should be aspirated and dispensed slowly due to the viscosity of the solution.

Some of the consumables should be stored and prepared as indicated in Table 2 below.

TABLE 2

Storage and preparation of consumables

| Item | Storage | Instructions |
|---|---|---|
| EMX | −25° C. to −15° C. | Thaw at room temperature, and then place on ice. Return to storage after use. |
| BMX | −25° C. to −15° C. | Thaw at room temperature, and then place on ice. Return to storage after use. |
| RSB | 2° C. to 8° C. | Let stand for 30 min to bring to room temperature. |
| SPB | 2° C. to 8° C. | Let stand for 30 min to bring to room temperature. |

The following EMX program may be saved on the thermal cycler: (i) choose the preheat lid option and set to 100° C.; (ii) 37° C. for 30 mins; (iii) 75° C. for 10 mins; and (iv) hold at 4° C.

The following BMX program may be saved on the thermal cycler: (i) choose the preheat lid option and set to 100° C.; (ii) 38° C. for 20 mins; (iii) 60° C. for 20 mins; and (iv) hold at 4° C.

For the exonuclease only treatment, the samples may be treated as follows: (i) centrifuge EMX at 600×g for 5 seconds; (ii) add 27 μl of DNA library sample pool to PCR tube; (iii) add 5 μl EMX to each sample in each PCR tube and then mix thoroughly by pipetting up and down; (iv) incubate by placing on the thermal cycler and running the EMX program. Each tube contains 32 μl.

For the exonuclease plus 3' blocking treatment, the samples may be treated as follows: (i) centrifuge EMX at 600×g for 5 seconds; (ii) add 27 μl of DNA library sample pool to PCR tube; (iii) add 5 μl EMX to each sample in each PCR tube and then mix thoroughly by pipetting up and down; (iv) incubate by placing on the thermal cycler and running the EMX program; (v) centrifuge BMX at 600×g for 5 seconds; (vi) add 32 μl BMX directly to each exonuclease reaction in each PCR tube and then mix thoroughly by pipetting up and down; and (vii) incubate by placing on the thermal cycler and running the BMX program. Each tube contains 64 μl.

The treated pooled sample may be cleaned up as follows: (1) vortex SPB until well-dispersed;

(2) add 60 μl SPB to each sample treatment tube and mix thoroughly by pipetting up and down; (3) incubate at room temperature for 5 minutes; (4) place on a magnetic stand and wait until the liquid is clear (2-5 minutes); (5) remove and discard all supernatant from each tube; (6) wash 2 times as follows: (a) add 200 μl freshly prepared 80% EtOH to each tube, (b) incubate on the magnetic stand for 30 seconds, and (c) remove and discard all supernatant from each tube; (7) use a 20 μl pipette to remove residual EtOH from each tube; (8) air-dry on the magnetic stand for 5 minutes; (9) add 22.5 μl RSB to each tube; (10) remove from the magnetic stand and then mix thoroughly by pipetting up and down; (11) incubate at room temperature for 2 minutes; (12) place on a magnetic stand and wait until the liquid is clear (2-5 minutes); (13) transfer 20 μl supernatant to a new tube; (14) quantify libraries if required and proceed onto standard clustering for the HiSeq® 4000 platform starting with NaOH denaturation step; and (15) store at −25° C. to −15° C. if not clustering immediately.

Example 2: Reduction of Index Hopping by Exonuclease Treatment with 3' Blocking of Indexed Libraries The treatment protocol set forth above in Example 1 was applied in combination with the following materials, equipment and methods for clustering and sequencing on Illumina platform.

Experimental conditions: (1) Human 450 bp NA12878 (Coriell Institute) TrueSeq® PCR-Free library loaded at 300 pM; (2) HiSeq® X instrument and Illumina SBS chemistry according to manufacturer's instructions; (3) 550 nm ILS v3 flow cell; (4) ExAmp amplification as previously described; and (5) 50% adapter spike-in: free forked adapter from the Illumina dual adapter plate (DAP) spiked into template library prior to denaturation, neutralization, ExAmp mix addition and clustering.

Figure 13:
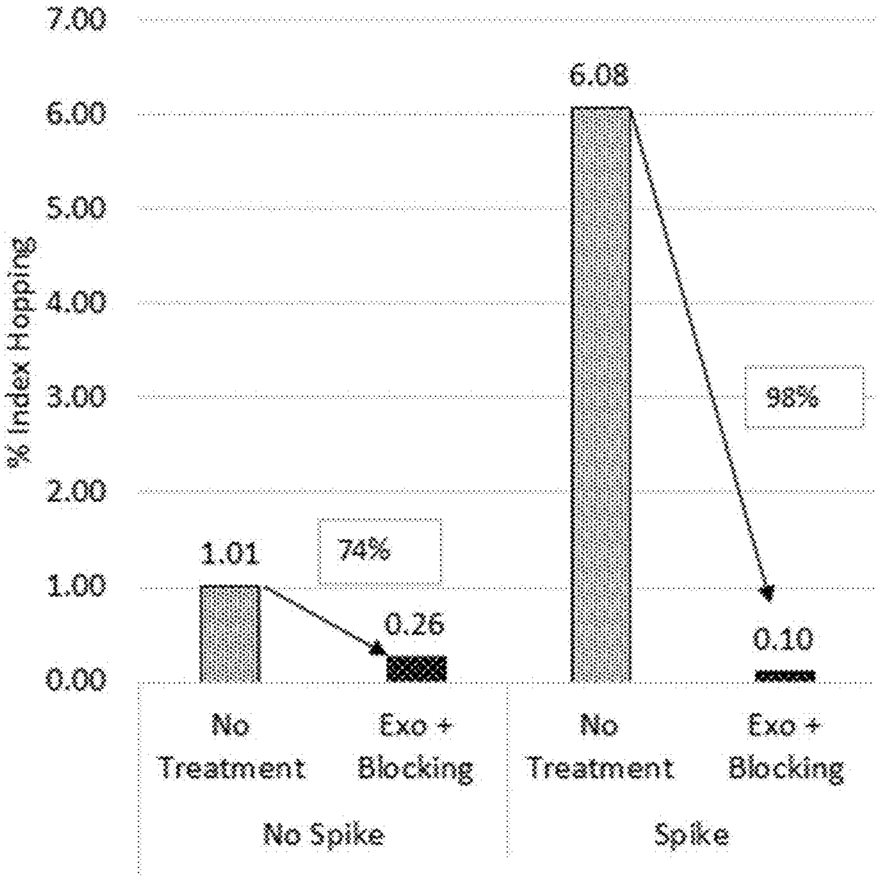

Results of this experiment are summarized in Table 3 below and FIG. 13.

TABLE 3

Reduction of index hopping by exonuclease treatment with 3' blocking

| | Adapter | Index hopping (% of PF clusters) | |
|---|---|---|---|
| Library | spike | No Treatment | Exo + 3' Block |
| TruSeq ® PCR-Free | None | 1.01% | 0.26% |
| | Spike | 6.08% | 0.10% |

As illustrated above, index hopping was decreased with exonuclease treatment combined with 3' blocking of DNA libraries.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

In addition to the documents already cited in this application, reference is hereby made to three provisional patent applications identically entitled "Compositions and methods for improving sample identification in indexed nucleic acid libraries" that are being filed concurrently (U.S. Prov. Appl. Ser. Nos. 62/488,824, 62/488,830, and 62/488,833. The entire contents of these applications are also incorporated herein by reference.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

What is claimed is:

1. A composition comprising:

a first plurality of adapter-target-adapter molecules comprising double-stranded target fragments isolated from a first source, wherein the adapter comprises a first sample-specific universal adapter, wherein the first sample-specific universal adapter comprises (i) a region of double stranded nucleic acid, and (ii) a region of single-stranded non-complementary nucleic acid strands comprising at least one universal primer binding site, wherein the first sample-specific universal adapter further comprises a first set of sample-specific tag sequences that differentiates the first plurality of adapter-target-adapter molecules from adapter-target-adapter molecules originating from a different source, the first set of sample-specific tag sequences present in the single stranded non-complementary nucleic acid strands, and an exonuclease, wherein the exonuclease does not comprise a DNA polymerase activity.

2. The composition of claim 1, further comprising first sample-specific universal adapters not attached to a target fragment.

3. The composition of claim 1, wherein the exonuclease comprises a 5' to 3' DNA exonuclease activity that is biased for double stranded DNA that comprises a 5' phosphate at the 5' end of the region of double stranded nucleic acid.

4. The composition of claim 3, wherein the exonuclease is lambda exonuclease.

5. The composition of claim 1, wherein the exonuclease comprises a 3' to 5' DNA exonuclease activity that is biased for double stranded DNA that is blunt ended and/or has a recessed 3' terminus.

6. The composition of claim 1, the composition further comprising a second plurality of adapter-target-adapter molecules comprising double-stranded target fragments isolated from a second source, wherein the adapter comprises a second sample-specific universal adapter that comprises a second set of sample-specific tag sequences that differentiates the first and second pluralities of adapter-target-adapter molecules.

7. The composition of claim 6, wherein 3' ends of the first and second pluralities of adapter-target-adapter molecules, or a combination thereof, are blocked.

8. The composition of claim 2, wherein 3' ends of the first sample-specific universal adapters not attached to a target fragment are blocked.

9. The composition of claim 1, further comprising terminal deoxynucleotidyl transferase, a ddNTP, a DNA polymerase, or a combination thereof.

10. A method, comprising:

providing a first solution of a plurality of double-stranded target fragments isolated from a first source;

ligating a first sample-specific universal adapter to both ends of the double-stranded target fragments from the first source to form a first plurality of adapter-target-adapter molecules, wherein each of the first plurality of adapter-target-adapter molecules comprises a target fragment flanked by the first sample-specific universal adapter, wherein the first sample-specific universal adapter comprises (i) a region of double stranded nucleic acid, and (ii) a region of single-stranded non-complementary nucleic acid strands comprising at least one universal primer binding site, wherein the first sample-specific universal adapter further comprises a first set of sample-specific tag sequences that differentiates the first plurality of adapter-target- adapter molecules from adapter-target-adapter molecules originating from a different source, the first set of sample-specific tag sequences present in the single stranded non-complementary nucleic acid strands, and wherein the ligating covalently attaches the region of double stranded nucleic acid of the first sample-specific universal adapter to each end of the double-stranded target fragments from the first source; and contacting the solution with an exonuclease, wherein the exonuclease comprises a 5' to 3' DNA exonuclease activity that is biased for double stranded DNA, wherein the exonuclease does not comprise a DNA polymerase activity, wherein the exonuclease selectively degrades first sample-specific universal adapters present in the first solution not ligated to a target fragment.

11. The method of claim 10, wherein the exonuclease comprises a 5' to 3' DNA exonuclease activity that is biased for double stranded DNA that comprises a 5' phosphate at the 5' end of the region of double stranded nucleic acid.

12. The method of claim 11, wherein the exonuclease is lambda exonuclease.

13. The method of claim 10, further comprising:

providing a second solution of a plurality of double-stranded target fragments isolated from a second source;

ligating a second sample-specific universal adapter to both ends of the double-stranded target fragments from the second source to form a second plurality of adapter-target-adapter molecules, wherein each of the second plurality of adapter-target-adapter molecules comprises a target fragment from the second source flanked by the second sample-specific universal adapter, wherein the second sample-specific universal adapter comprises (i) a region of double stranded nucleic acid, and (ii) a region of single-stranded non-complementary nucleic acid strands comprising at least one universal primer binding site, wherein the second sample-specific universal adapter further comprises a second set of sample-specific tag sequences that differentiates the second plurality of adapter-target-adapter molecules from adapter-target-adapter molecules originating from a different source, the second set of sample-specific tag sequences present in the single stranded non-complementary nucleic acid strands, and wherein the ligating covalently attaches the region of double stranded nucleic acid of the second sample-specific universal adapter to each end of the double-stranded target fragments from the second source; and contacting the solution with an exonuclease, wherein the exonuclease comprises a 5' to 3' DNA exonuclease activity that is biased for double stranded DNA, wherein the exonuclease selectively degrades second sample-specific universal adapters present in the second solution not ligated to a target fragment.

14. The method of claim 13, further comprising blocking 3' ends of the first and second pluralities of adapter-target-adapter molecules.

15. The method of claim 14, wherein the blocking comprises enzymatically incorporating a dideoxynucleotide onto the 3' ends of the first and second pluralities of adapter-target-adapter molecules and the 3' ends of the first and second sample-specific universal adapters that are not attached to a target fragment.

16. The method of claim 13, further comprising:

providing a surface comprising a plurality of amplification sites, wherein the amplification sites comprise at least two populations of attached single stranded nuclei acids having a free 3' end, and contacting the surface comprising amplification sites with a mixture of the first and second pluralities of adapter-target-adapter molecules under conditions suitable to produce a plurality of amplification sites that each comprise a clonal population of amplicons from an individual adapter-target-adapter molecule.

17. A method, comprising:

providing a first solution of a plurality of double-stranded target fragments isolated from a first source;

ligating a first sample-specific universal adapter to both ends of the double-stranded target fragments from the first source to form a first plurality of adapter-target-adapter molecules, wherein each of the first plurality of adapter-target-adapter molecules comprises a target fragment flanked by the first sample-specific universal adapter, wherein the first sample-specific universal adapter comprises (i) a region of double stranded nucleic acid, and (ii) a region of single-stranded non-complementary nucleic acid strands comprising at least one universal primer binding site, wherein the first sample-specific universal adapter further comprises a first set of sample-specific tag sequences that differentiates the first plurality of adapter-target-adapter molecules from adapter-target-adapter molecules originating from a different source, the first set of sample-specific tag sequences present in the single stranded non-complementary nucleic acid strands, and wherein the ligating covalently attaches the region of double stranded nucleic acid of the first sample-specific universal adapter to each end of the double-stranded target fragments from the first source; and contacting the solution with an exonuclease, wherein the exonuclease comprises a 3' to 5' exonuclease activity that is biased for double stranded DNA having a blunt or recessed 3' terminus, wherein the exonuclease does not comprise a DNA polymerase activity, wherein the ligating also forms a plurality of incomplete products comprising adapter-target molecules, and wherein the exonuclease selectively degrades adapter-target molecules and first sample-specific universal adapters present in the first solution not ligated to a target fragment.

18. The method of claim 17, wherein the exonuclease is exonuclease III.

19. The method of claim 17, wherein the region of double stranded nucleic acid distal to the region of single-stranded non-complementary nucleic acid strands terminates as a blunt end structure.

20. The method of claim 19, wherein the double-stranded target fragments comprise blunt end structures.

21. The method of claim 17, wherein the region of double stranded nucleic acid distal to the region of single-stranded non-complementary nucleic acid strands terminates as a 3' overhang structure.

22. The method of claim 17, further comprising:

providing a second solution of a plurality of double-stranded target fragments isolated from a second source;

ligating a second sample-specific universal adapter to both ends of the double-stranded target fragments from the second source to form a second plurality of adapter-target-adapter molecules, wherein each of the second plurality of adapter-target-adapter molecules comprises a target fragment from the second source flanked by the second sample-specific universal adapter, wherein the second sample-specific universal adapter comprises (i) a region of double stranded nucleic acid, and (ii) a region of single-stranded non-complementary nucleic acid strands comprising at least one universal primer binding site, wherein the second sample-specific universal adapter further comprises a second set of sample-specific tag sequences that differentiates the second plurality of adapter-target-adapter molecules from adapter-target-adapter molecules originating from a different source, the second set of sample-specific tag sequences present in the single stranded non-complementary nucleic acid strands, and wherein the ligating covalently attaches the region of double stranded nucleic acid of the second sample-specific universal adapter to each end of the double-stranded target fragments from the second source; and contacting the solution with an exonuclease, wherein the exonuclease comprises a 3' to 5' exonuclease activity that is biased for double stranded DNA having a blunt or 3' recessed terminus, wherein the exonuclease does not comprise a DNA polymerase activity, wherein the ligating also forms a plurality of incomplete products, wherein the incomplete products comprise adapter-target molecules, and wherein the exonuclease selectively degrades adapter-target molecules and second sample-specific universal adapters present in the second solution not ligated to a target fragment.

23. The method of claim 22, further comprising blocking 3' ends of the first and second pluralities of adapter-target-adapter molecules.

24. The method of claim 23, wherein the blocking comprises enzymatically incorporating a dideoxynucleotide onto the 3' ends of the first and second pluralities of adapter-target-adapter molecules and the 3' ends of the first and second sample-specific universal adapters that are not attached to a target fragment.

25. The method of claim 22, further comprising:

providing a surface comprising a plurality of amplification sites, wherein the amplification sites comprise at least two populations of attached single stranded nuclei acids having a free 3' end, and contacting the surface comprising amplification sites with a mixture of the first and second pluralities of adapter-target-adapter molecules under conditions suitable to produce a plurality of amplification sites that each comprise a clonal population of amplicons from an individual adapter-target-adapter molecule.

* * * * *